United States Patent
Lee et al.

(10) Patent No.: US 10,943,312 B2
(45) Date of Patent: Mar. 9, 2021

(54) RESTAURANT MATCHING AND FILTERING FOR USE IN A HEALTH TRACKING SYSTEM

(71) Applicant: Under Armour, Inc., Baltimore, MD (US)

(72) Inventors: Chul Lee, San Francisco, CA (US); Yi Qiang, San Francisco, CA (US)

(73) Assignee: MyFitnessPal, Inc., San Francisco, CA (US)

(\*) Notice: Subject to any disclaimer, the term of this patent is extended or adjusted under 35 U.S.C. 154(b) by 418 days.

(21) Appl. No.: 15/723,508

(22) Filed: Oct. 3, 2017

(65) Prior Publication Data

US 2018/0025446 A1 Jan. 25, 2018

Related U.S. Application Data

(63) Continuation-in-part of application No. 14/925,684, filed on Oct. 28, 2015, now Pat. No. 10,387,931.

(60) Provisional application No. 62/403,591, filed on Oct. 3, 2016.

(51) Int. Cl.
*G06Q 50/12* (2012.01)
*G06Q 30/06* (2012.01)
*A23L 33/00* (2016.01)
*G01S 19/42* (2010.01)

(52) U.S. Cl.
CPC .............. *G06Q 50/12* (2013.01); *A23L 33/30* (2016.08); *G06Q 30/0621* (2013.01); *G06Q 30/0623* (2013.01); *A23V 2002/00* (2013.01); *G01S 19/42* (2013.01)

(58) Field of Classification Search
CPC ........................... G06Q 50/12; G06Q 30/0621

USPC .......................................................... 705/15
See application file for complete search history.

(56) References Cited

U.S. PATENT DOCUMENTS

| | | | |
|---|---|---|---|
| 7,680,690 B1 * | 3/2010 | Catalano | G06Q 30/02 186/38 |
| 8,626,796 B2 | 1/2014 | McBride | |
| 8,719,244 B1 | 5/2014 | Pasca | |
| 9,070,175 B2 * | 6/2015 | Hurst | G06Q 50/12 |

(Continued)

OTHER PUBLICATIONS

Koga, Hisashi et al., Fast Agglomerative Hierarchical Clustering Algorithm using Locality-Sensitive Hashing, Knowledge and Information Systems, 12.1, 2007, pp. 25-53, Springer-Verlag London Ltd.

(Continued)

*Primary Examiner* — Florian M Zeender
*Assistant Examiner* — Christopher R Buchanan
(74) *Attorney, Agent, or Firm* — Maginot, Moore & Beck LLP

(57) ABSTRACT

A system and method of providing nutritional data for a user is disclosed herein. The method includes receiving a selected restaurant from a health tracking device, and providing menu data for the user based on the selected restaurant. The method further includes receiving a selected menu item from the health tracking device, associating the selected menu item with a plurality of food items in a database, and providing the plurality of food items for the user. Furthermore, the method includes receiving a selected one of the plurality of food items from the health tracking device, and providing nutritional data based on the selected one of the plurality of food items.

20 Claims, 15 Drawing Sheets

(56) References Cited

U.S. PATENT DOCUMENTS

| | | |
|---|---|---|
| 9,105,041 B2 | 6/2015 | Hurst |
| 9,104,915 B2 | 8/2015 | Conwell |
| 9,659,225 B2 | 5/2017 | Joshi |
| 2002/0107861 A1 | 8/2002 | Clendinning et al. |
| 2003/0208409 A1* | 11/2003 | Mault ................ G06F 19/3475 705/15 |
| 2004/0069313 A1* | 4/2004 | DeLaquil ................ G06Q 10/10 705/15 |
| 2004/0158494 A1* | 8/2004 | Suthar ................ G06Q 30/06 705/15 |
| 2007/0214052 A1* | 9/2007 | Kao ................ G06Q 50/12 705/15 |
| 2008/0033827 A1* | 2/2008 | Kuang ................ G06Q 50/22 705/15 |
| 2009/0300007 A1 | 12/2009 | Hiraoka |
| 2010/0088193 A1* | 4/2010 | White ................ G06Q 30/0601 705/26.1 |
| 2012/0233002 A1* | 9/2012 | Abujbara ................ G06Q 10/06 705/15 |
| 2013/0325640 A1* | 12/2013 | Morgan ................ G06Q 50/12 705/15 |
| 2015/0294292 A1* | 10/2015 | Michishita ................ G06Q 50/12 705/15 |
| 2015/0364057 A1* | 12/2015 | Catani ................ G09B 19/0092 434/127 |
| 2016/0071431 A1 | 3/2016 | Jain |
| 2016/0125446 A1* | 5/2016 | Gonen ................ G06Q 30/0226 705/14.27 |

OTHER PUBLICATIONS

Kontorovich, Aryeh and Ari Trachtenberg, String Reconciliation with Unknown Edit Distance, Information THeory Proceedings (ISIT), 2012, IEEE International Symposium.

Lambert, Bruce L. et al., Similarity As a Risk Factor in Drug-Name Confusion Errors: the Look-Alike (Orthographic) and Sound-Alike (Phonetic) Model, Medical Care, 1999, pp. 1214-1225.

Hochuli, Alexandra, Data Cleansing for Food Composition Data, Global Information Systems Group, Institute of Information Systems, Department of Computer Science, Apr. 7, 2014.

Bilenko, Mikhail et al., Adaptive Product Normalization: Using Online Learning for Record Linkage in Comparison Shopping, Proceedings of the 5th International Conference on Data Mining, Nov. 2005, pp. 58-65, Houston, TX.

Kennedy, Eileen T. et al., The healthy eating index: design and applications, Journal of the American Dietetic Association 95.10, 1995, pp. 1103-1108.

\* cited by examiner

RESTAURANT MATCHING AND FILTERING FOR USE IN A HEALTH TRACKING SYSTEM

CROSS-REFERENCE TO RELATED APPLICATIONS

This application is a continuation-in-part of and claims priority from U.S. patent application Ser. No. 14/925,684 entitled "Health Tracking System With Restaurant Matching," filed Oct. 28, 2015, and also claims priority from U.S. Provisional Patent Application No. 62/403,591 entitled "Restaurant Matching and Filtering for use in a Health Tracking System," filed Oct. 3, 2016, the entire contents of which are incorporated by reference herein.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

This document relates to the field health and fitness tracking devices, and particularly to devices configured to collect and display nutritional information for a user.

BACKGROUND

Health and fitness tracking devices are increasingly utilized by individuals interested in tracking metrics related to their personal health and fitness. These health and fitness tracking devices (which may also be referred to herein as "health tracking devices") typically include a user interface provided on a health tracking device such as a smartphone, laptop computer, or other computer. The user interface provides the user with any of various health, fitness and activity related data such as calorie and nutritional consumption, calorie expenditure, heart rate, distance travelled, steps taken, etc. Health tracking devices often use data collected from associated sensors worn by the user, such as heart rate monitors, step counters, stair counters, global positioning system ("GPS") tracking devices, as well as various other motion tracking and biometric monitoring devices. Such sensors are allow the user to easily track and automatically log activity information with the health tracking device. The term "health tracking system" as used herein refers to a health tracking system and/or health and fitness tracking system which is configured to make use of a health tracking device but which may or may not be used in association with any sensor device.

While activity data is relatively easy to enter into a health tracking device, challenges exist with entry of food and beverage consumption and related calorie and nutritional data. In particular, the user must manually log this data into the health tracking system in order for the system to properly monitor calorie and macronutrient consumption and related health concerns. This process of manually entering food and beverage consumption data into the system along with calorie and nutritional data is often time consuming and cumbersome. Moreover, it is often difficult for users to accurately determine the calorie and nutritional content of the foods they eat, so the calorie consumption and nutritional data entered into the health tracking system is often inaccurate.

In view of the foregoing, it would be advantageous to provide a health tracking system and related method that allows the user to more quickly and easily enter calorie consumption and nutritional content into a health tracking system. It would also be advantageous if such a system and method provided the user with more accurate calorie consumption and nutritional data for entry into the system in association with foods consumed by the user. Moreover, it would be advantageous if such a system and method could be used to limit the food choices to assist the user in making healthy food choices.

SUMMARY

In accordance with one exemplary aspect of the disclosure, there is provided a method of providing nutritional data to a user of a health tracking system. In one embodiment, the method comprises: (i) enabling the user to select a restaurant via a health tracking device of the health tracking system; (ii) generating first menu data based at least in part on the selected restaurant, the first menu data comprising a plurality of data records each having nutritional data associated therewith; (iii) enabling the user to enter a filtering metric by which the first menu data is filtered; and (iv) generating second menu data based at least in part on the filtered first menu data.

In another aspect, a non-transitory computer readable medium for operating a health tracking system is provided. In one embodiment, the computer-readable readable medium comprises a plurality of instructions stored thereon that, when executed by a processor, cause the processor to: (i) provide a selectable list of restaurants to a user; (ii) in response to a user's selection of one of the restaurants on the list, generate first menu data, the first menu data comprising a plurality of records, each record being comprising a text string representative of the consumable item to which the record relates and nutritional data associated to the consumable item; (iii) providing a mechanism to enable the user to filter the first menu data according to at least one of the text string and/or the nutritional data thereof; and (iv) in response to the user's filter, generate second menu data.

In yet another aspect of the disclosure, a network apparatus is provided. In one embodiment, the network apparatus is configured to provide menu data to a user of a health tracking device, and comprises: an interface configured to communicate to the health tracking device; a storage apparatus; and a processor configured to execute a computer application comprising a plurality of instructions which are configured to when executed, cause the network apparatus to: (i) generate menu data relating to one or more consumable items at a restaurant, the menu data including a first list of menu items and associated nutritional values; (ii) receive an indication from the user to filter the list of menu items to only those ones having a desired nutritional value; and (iii) generate a revised list of menu data for the restaurant based on the filter, the revised menu data including a second list of menu items that is a subset of the first list of menu items which have the desired nutritional value.

The above described features and advantages, as well as others, will become more readily apparent to those of ordinary skill in the art by reference to the following detailed description and accompanying drawings. While it would be desirable to provide a health tracking device and associated method that provides one or more of these or other advantageous features, the teachings disclosed herein extend to those embodiments which fall within the scope of the appended claims, regardless of whether they accomplish one or more of the above-mentioned advantages.

Figure 1:
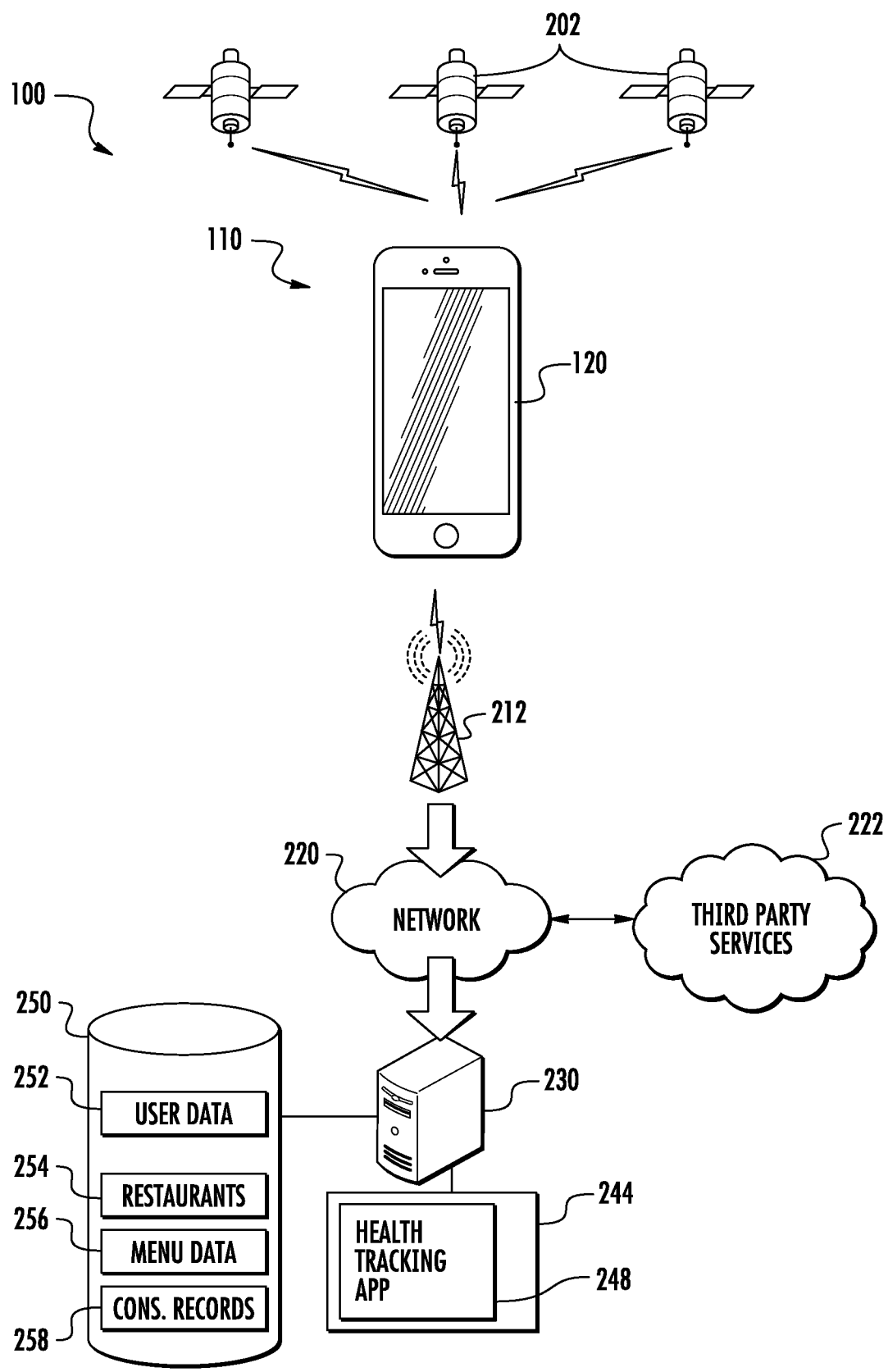
FIG. 1 is a block diagram illustrating an exemplary embodiment of a health tracking system including a personal electronics device in communication with a system server.

All Figures© Under Armour, Inc. 2016. All rights reserved.

DESCRIPTION

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as may normally occur to one skilled in the art which this disclosure pertains.

Disclosed embodiments include systems, apparatus, and methods associated with health and fitness tracking in general and, in particular, a system for collecting and displaying nutritional information to a user.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It is noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art will readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description is not to be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

As used herein, the term "consumable" or "consumable item" refers to foods, beverages, dietary supplements, vitamin supplements, medication, and other items for consumption. As used herein, the phrase "consumable record" or "consumable item record" refers to a data record comprising information relating to a particular consumable. Each consumable record comprises a plurality of data fields that relate to a particular consumable. In some embodiments, the consumable record includes a description field that includes data, such as a text string, that identifies or describes the particular consumable. In some embodiments, each consumable record includes fields for caloric content, macronutrients, micronutrients, serving size, and other nutrition and health information.

Exemplary Health Tracking System

With reference to FIG. 1, an exemplary embodiment of a health tracking system 100 is shown including functionality for enabling a user to log items in the health tracking system based on restaurant menus and associated filtering of the items on the restaurant menu. In the illustrated embodiment, the health tracking system 100 includes one or more health tracking devices 110 configured to communicate with a data processing system such as a system server 230 or other data processing system over a network 220, such as, e.g., the Internet.

The server 230 comprises a computerized device or data processing system configured to run one or more software applications on a processor thereof (e.g. the network-side health tracking program 248). The server 230 of the present embodiment is further configured to receive data relating to a selection of individual ones of a plurality of consumable records 258 from the health tracking devices 110. In one embodiment, the consumable records are each associated with nutritional data including caloric and macronutrient data relating to respective ones of a plurality of consumable items. The consumable records are stored at a storage apparatus or memory of the server 230 (e.g., consumable records 258).

The storage apparatus or memory of the server 230 is configured to store instructions including the network-side health tracking program 248 (which may also be referred to herein as the "health tracking application"), as well as a database 250 accessible by at least the health tracking program 248. The database 250 includes user profile data 252, restaurant records 254, menu records 256, and consumption records 258, as will be discussed in greater detail below with respect to FIG. 3. Alternatively, the server 230 may be in communication with a separate storage entity (not shown) for storage of one or more of the foregoing data and/or records.

The health tracking devices 110 (which may also be referred to herein as "health and fitness tracking devices") comprise any number of computerized apparatus which include a user interface such as, a smartphone, laptop computer, a tablet computer, a desktop computer, or other such device. In at least one embodiment, the user interface may comprise an LCD touch screen or the like, a mouse or other pointing device, a keyboard or other keypad, speakers, and a microphone, as will be recognized by those of ordinary skill in the art. The user interface enables the user to interact with at least one client-side health monitoring application configured to provide any of various health, fitness and activity related data such as food and nutritional consumption, calorie expenditure, sleep metrics, weight, body fat, heart rate, distance travelled, steps taken, etc. In order to connect to the network 220, as demonstrated in FIG. 1, the health tracking devices 110 are generally configured to utilize any of various wired or wireless communications components, infrastructures and systems, such as cell towers 212 of a mobile telephony network, wireless routers, Bluetooth®, near field communication (NFC), or physical cables. Health tracking devices 110 may use data collected from sensors associated to or in communication with the health tracking device 110, such as heart rate monitors, step counters, stair counters, global positioning system ("GPS") tracking devices, as well as various other motion tracking and biometric monitoring devices; alternatively, or in addition, a user may manually enter health related data. Such sensors allow the user to easily track and automatically log activity and/or consumption information with the health tracking device.

The health tracking devices 110 are configured to communicate with the system server 230 in order to enable: accessing and searching of the consumable records 258 stored thereat, display of the consumable records, provide additional consumable records, and/or enable the user to select individual ones of the displayed consumable records for the purposes of caloric and nutritional logging. In one embodiment, foregoing functions are performed via execution of one or more software applications at the server 200 (i.e., server or network-side applications) in communication with one or more complementary software applications at the health tracking devices 110 (i.e., client-side applications). For example, the health tracking program 248, running on the processor (of the server 230) may be utilized to accomplish the foregoing, as explained in further detail below. Alternatively, or in addition, the client-side software application for performing various functions necessary for the herein disclosed concepts may also be utilized (e.g., a health tracking application provided in the memory 138 of the exemplary health tracking device of FIG. 2, discussed in further detail below). Accordingly, it will be recognized that any of various processing described herein as being performed at the server 230 may alternatively be provided on a health tracking device 110, and vice-versa, in order to accomplish the desired functionality of the health tracking system 100, as described herein.

In one exemplary embodiment, each health tracking device 110 is configured to determine a user location and provide the user with information concerning nearby restaurants stored in the restaurant records 254. The health tracking device is configured to allow the user to view restaurant menus from the menu records 256, and select menu items from the restaurant menus. The system server 230 receives the selected menu items from the health tracking device 110 and matches each selected menu item with a number of consumable records 258 from the memory 234. Matched consumable records are presented to the user on the health tracking device 110. The user may select one of the consumable records on the health tracking device 102 in order to view nutritional information or log food consumption for a particular day, as will be discussed in greater detail below.

Exemplary Health Tracking Device

Figure 2:
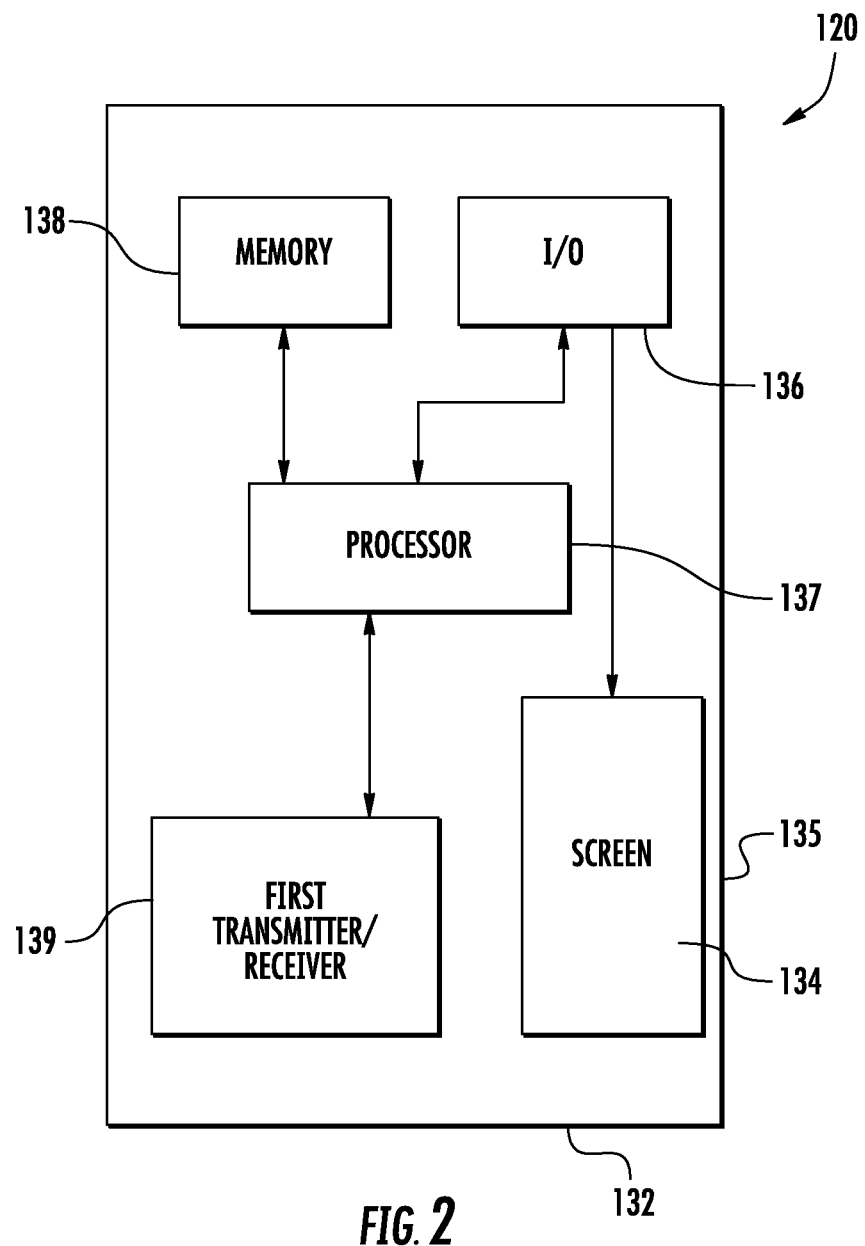
FIG. 2 is a block diagram of an exemplary personal electronics device for use in association with the health tracking system of FIG. 1.

With reference now to FIG. 2, in at least one embodiment the health tracking device 110 is a smartphone 120 and includes a display screen 134, an input/output (I/O) interface 136, a processor 137, a memory 138, and one or more transceivers 139. The smartphone 120 also includes a protective outer shell or housing 132 designed to retain and protects the electronic components positioned within the housing 132. The smartphone 120 also includes a rechargeable battery (not shown) configured to power the display screen 134, processor 137, transceivers 139 and various other the electronic components within the smartphone 120. As will be recognized by those of ordinary skill in the art, the components of the health tracking device 110 may vary depending on the type of display device used. Such alternative health tracking devices may include much of the same functionality and components as the smartphone 120 shown in FIGS. 1 and 2, but may not include all the same functionality or components.

The display screen 134 of the smartphone 120 may be an LED screen or any of various other screens appropriate for the personal electronic device. In at least one embodiment, the display screen 134 is an LED-backlit touchscreen that allows the user to make selections, type, or otherwise provide input directly on the screen using his or her finger or a stylus device. The I/O interface 136 of the smartphone 140 includes software and hardware configured to facilitate communications with the user. The I/O interface is in communication with the display screen 134 and is configured to visually display graphics, text and other data to the user via the display screen 134. In addition to the display screen 134, the I/O interface 136 may include additional hardware such as a microphone and speakers to facilitate audio communications with the user. As will be recognized by those of ordinary skill in the art, the components of the health tracking device 110 may vary depending on the type of display device used. Alternative health tracking devices, such as a laptop or a desktop computer, may include much of the same functionality and components as the smartphone 120 shown in FIG. 2 and/or may include others not listed.

The processor 137 of the smartphone 120 may be any of various processors as will be recognized by those of ordinary skill in the art. The processor 137 is connected to the I/O interface 136, the memory 138, and the transceivers 139, and is configured to deliver data to and receive data from each of these components. The memory 138 is configured to store information, including data and instructions (e.g., a client-side health tracking application) for execution by the processor 137. It will be recognized by those of ordinary skill in the art that a "processor" includes any hardware system, hardware mechanism or hardware component that processes data, signals or other information. A processor can include a system with a central processing unit, multiple processing units, dedicated circuitry for achieving functionality, or other systems.

As noted above, the memory 138 of the smartphone 210 includes both program instructions and data. For example, the memory 138 may include program instructions for a graphical user interface configured to provide a client-side health tracking application. The memory 138 may further be configured to store certain user data, including user profile data such as, e.g., user gender, height, weight, user identifier, password, etc. Additionally, user data such as activity and other health related data (e.g., data collected from one or more sensors and/or manually entered) may be stored either at the device 120 or at a separate storage entity (not shown) in communication therewith. The data may include any of various types of data that may be useful to the computing device and any associated applications. In the embodiments disclosed herein, the data may include restaurant data, menu data, and consumable data including nutritional data for foods served at any of various restaurants. The instructions may include a graphical user interface configured to provide a health tracking application on the smartphone 120. The processor 137 is configured to read the program instructions from the memory 138 and execute the program instructions to provide the health tracking application to the user so for the purpose of performing health and fitness related tasks for the user, including displaying, modifying, and analyzing the user data.

The memory 138 that retains the data and instructions may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. Portions of the system and methods described herein may be implemented in suitable software code that may reside within the memory as software or firmware. Alternatively, or in addition, the software (such as e.g., the client-side health tracking application 316) may be downloaded from a network location, such as via the Internet.

A computer program product implementing an embodiment disclosed herein may therefore comprise one or more computer-readable storage media storing computer instructions translatable by a processor to provide an embodiment of a system or perform an embodiment of a method disclosed herein. Computer instructions may be provided by lines of code in any of various languages as will be recognized by those of ordinary skill in the art. A "non-transient computer-readable medium" may be any type of data storage medium that can store computer instructions, including, but not limited to the memory devices discussed above.

With continued reference to FIG. 2, the one or more transceivers 139 may be any of various transceivers configured for wireless or wired communication with other electronic devices, including the ability to send communication signals and receive communication signals. The transceivers 139 may include different types of transceivers configured to communicate with different networks and systems. Such transceivers are well known and will be recognized by those of ordinary skill in the art. The transceivers typically perform wireless communications. However, in at least one embodiment, the transmitters may be used in association with data ports requiring a physical (i.e., wired) connection to another device prior to transmission of the data.

In at least one embodiment, the one or more transceivers 139 are configured to allow the smartphone 120 to perform wireless communications with a wireless telephony network, as will be recognized by those of ordinary skill in the art. The wireless telephony network may comprise any of several known or future network types. For example, the wireless telephony network may comprise commonly used cellular phone networks using CDMA, GSM or FDMA communication schemes, as well as various other current or future wireless telecommunications arrangements.

In at least one embodiment, the transceivers 139 further include GPS receivers configured to receive GPS signals from GPS satellites 202 (shown in FIG. 1). Accordingly, the smartphone 120 or other health tracking device may be a geo-position enabled device configured to determine its location based on received signals utilized by the health tracking system 100. While the smartphone 120 is described herein as being a GPS-enabled device, it will be appreciated that in other embodiments, other geo-position devices may be provided utilizing signals and technologies other than GPS.

In addition to transceivers configured to communicate with the cellular towers 212 of a wireless telephony network, and receive signals from GPS satellites 202, the transceivers 139 may also be configured to communicate with any of various other electronics devices and networks using any of various communication schemes. For example, the transceivers 139 may also be configured to allow the smartphone 120 to communicate with any of various local area networks using WiFi, Bluetooth® or any of various other communications schemes.

In at least one embodiment, the smartphone 120 is configured to collect sensor data from one or more sensors which are associated with the user. Such sensors may include sensors worn or carried by the user separate from the smartphone 120, or sensors included on the smartphone 120. Exemplary sensors may include heart rate monitors, accelerometers, breathing sensor, temperature sensors, or any of various other sensors typically associated with athletic activity. Exemplary sensor data may include heart rate, power, motion, movement, speed, range, distance, acceleration data, etc. Sensor data may include physiological data (e.g., heart rate, breathing rate, temperature, etc.) or contextual readings or calculations (e.g., distance travelled, acceleration, etc.), or estimates of such associated with various physical activities of the user (e.g., calories burned, etc.).

Exemplary System Server

Figure 3:
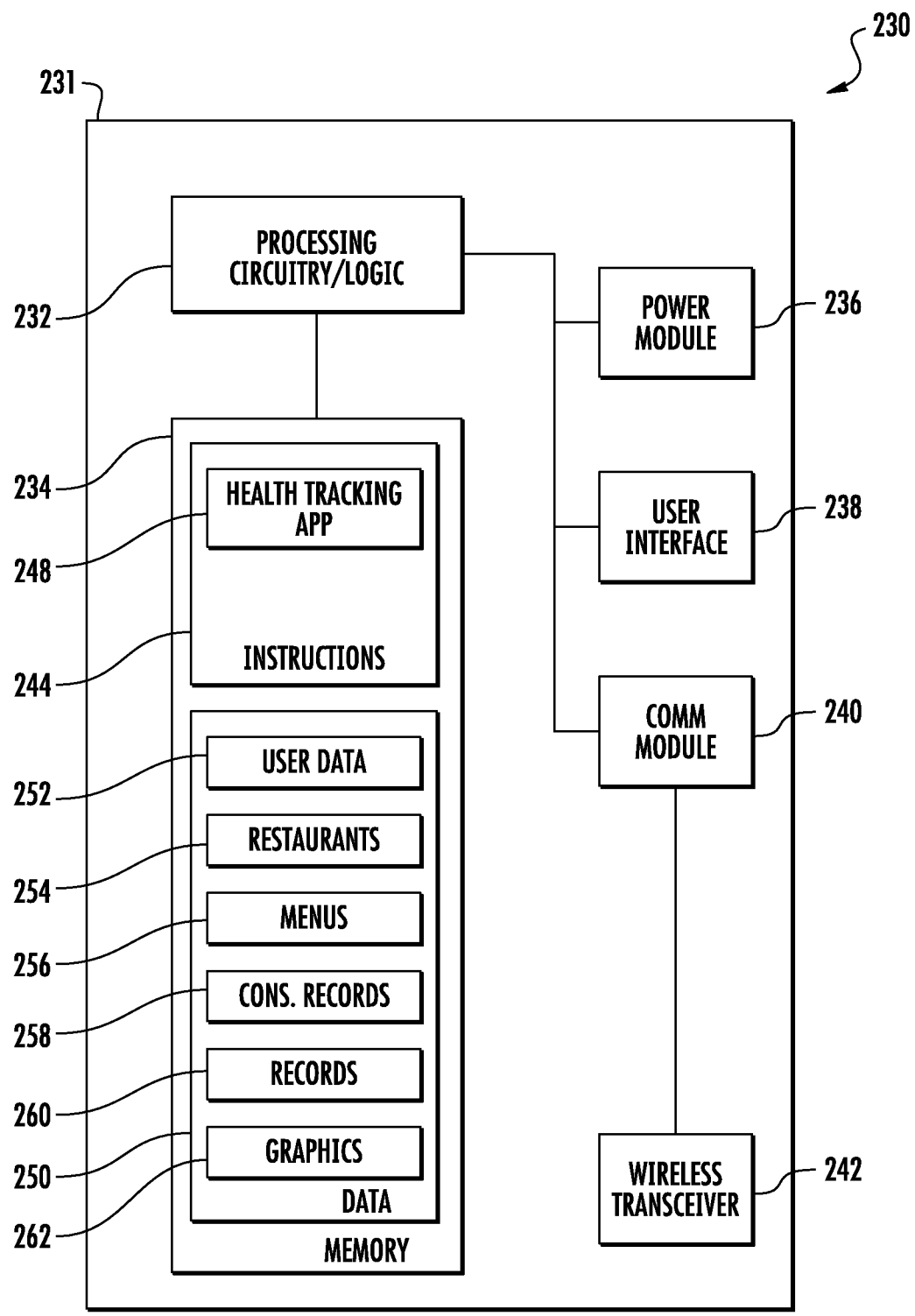
FIG. 3 is a block diagram of an exemplary system server for use in association with the health tracking system of FIG. 1.

With reference now to FIG. 3, a block diagram of an exemplary embodiment of the system server 230 of FIG. 1 is shown. It should be appreciated that the embodiment of the system server 230 shown in FIG. 3 is only one exemplary embodiment of a system server 230. As such, the exemplary embodiment of the system server 230 of FIG. 3 is merely representative of any of various manners or configurations of system servers or other data processing systems that are operative in the manner set forth herein.

The system server 230 of FIG. 3 is typically provided in a housing, cabinet or the like 231 that is configured in a typical manner for a server or related computing device. The system server 230 includes processing circuitry/logic 232, memory 234, a power module 236, a user interface 238, a network communications module 240, and a wireless transceiver 242.

The processing circuitry/logic 232 is operative, configured and/or adapted to operate the system server 230 including the features, functionality, characteristics and/or the like as described herein. To this end, the processing circuit 232 is operably connected to the memory 234, the power module 236, the user interface 238, the network communications module 240, and the wireless transceiver 242. The processing circuitry/logic 232 is typically under the control of program instructions 244. The program instructions include a health tracking application 248 as explained in further detail below. In addition to storing the instructions 244, the memory 234 also stores data 250 for use by the collection application 244. The data 250 includes user data 252, restaurant records 254, a menu records 256, a consumable records 258, operational records 260 and graphics 262, explained in further detail below. In an alternative embodiment, one or more of the data 250 is stored at a separate storage apparatus (not shown) in communication with the server 230.

With continued reference to FIG. 3, the power module 236 of the system server 230 is operative, adapted and/or configured to supply appropriate electricity to the system server 230 (i.e., including the various components of the system server 230). The power module 236 may operate on standard 120 volt AC electricity, but may alternatively operate on other AC voltages or include DC power supplied by a battery or batteries.

The network communication module 240 of the system server 230 allows for communication with any of various devices using various means. In particular, the network communications module 240 includes a wide area network port that allows for communications with remote computers over the Internet (e.g., network 220 of FIG. 1). Alternatively, the system server 230 communicates with the network 220 via a modem and/or router of the local area network. The network communications module 240 further includes a local area network port that allows for communication with any of various local computers housed in the same or nearby facility. In at least one embodiment, the local area network port is equipped with a WiFi transceiver 242 or other wireless communications device. Accordingly, it will be appreciated that communications with the system server 230 may occur via wired communications or via the wireless communications. Communications may be accomplished using any of various known communications protocols. In the embodiment of FIG. 3, the wireless transceiver is identified as a WiFi transceiver 242, but it will be recognized that the wireless transceiver could use a different communications protocol.

The system server 230 may be accessed locally. To facilitate local access, the system server 230 includes an interactive user interface 238. Via interface 228, the user may access the instructions, including the health tracking application 248, and may collect data from and store data to the memory 234. In at least one embodiment, the user interface 238 may suitably include an LCD type screen or the like, a mouse or other pointing device, a keyboard or other keypad, speakers, and a microphone, as will be recognized by those of ordinary skill in the art. Accordingly, the user interface 238 is configured to provide an administrator or other authorized user with access to the memory 234 and allow the authorized user to amend, manipulate and display information contained within the memory.

As mentioned above, the memory 234 includes various programs and other instructions 244 that may be executed by the processor 232. In particular, the memory 234 of the system server 230 of FIG. 3 includes the health tracking application 248 (which may also be referred to herein as a "health tracking program" and/or the "network-side health tracking application"). The health tracking application 248 is configured to control the system server 230 in order to allow a human to obtain nutritional data related to any of various consumables. Execution of the health tracking application 248 by the processor 232 results in signals being sent to and received from the user interface 238 and the communications module 240 (for further delivery to a user device such as a health tracking device 110), in order to allow a user receive and update the information in the consumable records 258. The health tracking application 248 is configured to provide various graphical views and screen arrangements to be displayed to a user on a health tracking device 110. Examples of such graphical views and screen arrangements for display on a health tracking device 110 are provided in FIGS. 4-9 and 11-19, as discussed in further detail below. While a brief description of various features of the exemplary health tracking application 248 is provided in the paragraphs below, it should be appreciated that the health tracking system 100 described herein is only an exemplary form or configuration for the health tracking system.

As noted previously, the data 250 in the memory 234 includes user data 252, restaurant records 254, menu records 256, consumable records 258, operational records 260, and graphics 262. The user data 252 includes user profile data and corresponding consumable logs for each user of the health tracking system 100. The user profile data includes demographic information for the users, such as name, age, gender, height, weight, performance or activity level (e.g., beginner, intermediate, professional, sedentary, active, etc.) and/or other information relating to the user. Each user profile may also include one or more goals. The user's goals may be provided as any number of different types of goals, such as activity goals, dietary goals, weight-loss goals, or any of various other health-related goals. The user goals may be long-term or short term goals. As an example, in at least one embodiment, the user goals may limit caloric intake for each meal for the user to a predetermined calorie limit.

In at least one embodiment, the consumable logs include a consumable diary/log for each user. The consumable diary/log allows the user to track items that are consumed by the user over a day, a period of days, etc., and any nutritional data associated with each item consumed. For example, the consumable diary/log may allow the user to enter, via a user device 110, a particular item that is or was consumed by the user and has nutritional data relating thereto stored so that the user may keep track of e.g., the associated calories, macronutrients, micronutrients, sugar, fiber, and/or any of various other nutritional data associated with the consumables entered by the user in the consumable diary/log. Each consumable entered into the consumable diary/log may be associated with a particular day and, even further, to a particular meal within that day. In some embodiments, the user data 252 further includes various activity and fitness data collected by sensors (not shown) associated with the health tracking devices 110.

In an alternative embodiment, the foregoing profile data may be stored at a storage entity separate from, yet in communication with, the server 230. For example, a centralized server may be provided which is configured to store all data relating to an individual user in one storage area (including workout data, nutrition/consumption data, profile data, etc.).

With continued reference to FIG. 3, in addition to the user data 222, the data stored in the memory 234 also includes restaurant records 254, menu records 256, consumable records 258, operational records 260, and graphics 262. The restaurant records 254 includes restaurant data concerning a number of different restaurants. The restaurant data may include any of various types of information concerning restaurants such as restaurant name, geographic location (e.g., longitude latitude data), restaurant type (e.g., bar, fast food, fine dining, Mexican food, Chinese food, sandwich shop, etc.), and restaurant menu types (e.g., breakfast, lunch, dinner, drinks, desserts, etc.). As explained in further detail below, the user may be presented with restaurant data based on any of various conditions, such as user proximity to the restaurant, a search for the restaurant name or type, etc. The user may select a particular restaurant from the restaurant data. While FIGS. 1 and 3 show the restaurant records 254 as being provided on the system server 230, it will be recognized that in alternative embodiments the restaurant records 254 may be provided at any of various locations, including third party databases and related remote memory locations in communication with the server 230. In at least one embodiment, the health tracking application 248 is configured to access such third party databases using third party services 222 available via the network 220, as shown in FIG. 1. In such embodiment, the health tracking application 248 may utilize any number of application programming interfaces (APIs) to access the data in the third party databases and incorporate such information for use in the health tracking application 248. In some embodiments, and depending on available licenses, the data obtained using the third party services 222 (including restaurant data) may be copied and saved to the memory 234 of the system server 230 such that a partial or complete copy of the remote restaurant records is maintained on the system server 230. In other embodiments, each time data from the remote memory location is needed, the health tracking application 248 uses the appropriate APIs to gather the required information from the third party databases. Any of various third party service providers and associated restaurant records and APIs may be used by the health tracking application to obtain the restaurant data. Examples of such third party service providers capable of providing restaurant data include Foursquare® Labs, Inc. of New York, N.Y., and Yelp®, Inc. of San Francisco, Calif. In at least one embodiment, restaurant information may also be provided by individual restaurants.

The menu records 256 provide menu data for each restaurant in the restaurant records 254. In at least one embodiment, each menu record includes menu data in the form of a restaurant identifier, a menu identifier and a list of associated menu items. The restaurant identifier provides a name, code or other identifier for a particular restaurant (e.g., Starbucks® at 870 $7^{th}$ Ave., New York, N.Y.). The menu identifier provides a name, code or other identifier for the specific menu for the restaurant (e.g., breakfast, lunch, dinner, anytime, etc.). Each menu record includes a number of menu items. The term "menu item" as used herein refers to data concerning a consumable listed on a particular menu. For example, each menu record 256 may include a text name for each associated menu item (e.g., "Chicken Cobb Salad"), a brief listing of additional information for the menu item (e.g., "500 calories"), a photo of the menu item, or other information intended to quickly convey information about the menu item to the user. In at least one embodiment, a menu item identifies a particular consumable by name, calorie content, macronutrient content, and additional data. In another embodiment, a menu item may be provided by a cross-reference to one of the consumable records 258 which, in turn, provides data for the menu item, including the name of the consumable, calorie content, macronutrient content, and additional data. Each menu record may also include data concerning menu categories or headings. For example, if a restaurant has a dinner menu, that dinner menu may include seven menu items under the "Appetizer" heading, five menu items under the "Salad" heading, ten menu items under the "Sides" heading, and eight menu items under the "Entrées" heading. Menu items are not editable by users of the health tracking system, and may only be edited by authorized personnel having editing privileges within the menu records 256.

Data for each menu item is retained in the menu records 256 and/or the consumable records 258. As explained in further detail below, after the user chooses a particular menu to view (e.g., Applebee's® Dinner Menu), the user may then select one of the menu items from such menu. While FIGS. 1 and 3 show the menu records 256 as being provided on the system server 230, it will be recognized that in alternative embodiments the menu records 256 may be provided at any of various locations, including third party databases and related remote memory locations. In at least one embodiment, the health tracking application 248 is configured to access such third party databases using third party services 222 available via the network 220, as shown in FIG. 1. In such embodiment, the health tracking application 248 may utilize any number of APIs to access the data in the third party databases and incorporate such information for use in the health tracking application 248. In some embodiments, and depending on available licenses, the data obtained using the third party services 222 (including the menu items) may be copied and saved to the memory 234 of the system server 230 such that a partial or complete copy of the remote menu records is maintained on the system server 230. In other embodiments, each time data from the remote memory location is needed, the health tracking application 248 uses the appropriate APIs to gather the required information from the third party databases. Any of various third party service providers and associated restaurant records and APIs may be used by the health tracking application to obtain the restaurant data, including the exemplary third party service provides discussed above in association with the restaurants database. In at least one embodiment, menu information may also be provided by individual restaurants.

With continued reference to FIG. 3, the consumable records 258 are also stored in the memory 234. The phrase "consumable record" refers to a database record that relates to a particular consumable item such as, for example, a menu item (e.g., "McDonald's® Quarter Pounder With Cheese"), a generic food item (e.g., "banana"), a recipe (e.g., "chicken tetrazzini"), etc. In the disclosed embodiment, each of the consumable records includes a number of fields including, for example, a name for the consumable item, summary information about the consumable item, and detailed nutritional information about the consumable item. Detailed information about a consumable item may include one or more of: serving size, calories, ingredients, or any other nutritional information about the consumable. For example, the nutritional information may include information that may be provided on USDA food labels or state-regulated food labels (e.g., vitamin and mineral content, fat content, cholesterol content, protein content, sugar content, carbohydrate content, fiber content, organic contents, etc.). The summary information about the consumable item may include a subset of the detailed information listed above. For example, the summary information about the consumable may only include serving size and calorie information. The various fields of each consumable record may be populated by data from any user or third party data providers. Therefore, it will be recognized that in at least some embodiments, consumable records 258 may have been entered by any of various sources including an administrator or operator of the health tracking system 100, commercial food providers (e.g., food distributors, restaurant owners, etc.), and/or users of the health tracking system 100.

In at least one embodiment, the data maintained for one or more menu items in the menu records 256 may resemble or be identical to data maintained for one or more consumable items in the consumable records 258. However, as discussed previously, in at least one embodiment, the menu records 256 simply reference one or more consumable records 258. Additionally, in at least one embodiment, no menu item in a particular menu record is exclusively associated with a single consumable record. Instead, as explained in further detail below, each time a menu item from a menu record 256 is selected by a user, the system server 230 matches a number of consumable records 258 with the selected menu item, and one of those consumable records may then be selected by the user. While no menu item is exclusively associated with a single consumable record, the number of times a menu item is matched with a consumable record and then selected by a user is also maintained as data within the memory of the system server 230 or other data processing system. The number of times that a consumable record has been selected by a user in association with a menu item may then be used by the system 100 to determine whether a consumable record should be a match with a selected menu item when determining future consumable record matches for the menu item.

The operational records 260 include current and historical data stored by the system server 230 in association with operation of the system server 230, execution of the health tracking application 248, and manipulation of data 250 within the memory 234. For example, the operational records 260 may include information concerning amendments made to any of various consumable records 258. The operational records 260 may also include other information related to the control and operation of the system server 230, including statistical, logging, licensing, and historical information.

In one embodiment, graphical views 262 are provided at the server 230 which are pushed to the health tracking device 110 for display thereat of various screen arrangements. Examples of such screens for display on a health tracking device 110 are provided in FIGS. 4-9 and 11-19, discussed in further detail below.

While the system server 230 has been explained in the foregoing embodiment as housing the health tracking application 248 and the various records and databases in the memory 234, it will be recognized that these components may be retained in one or more other locations in association with the health tracking system 100. For example, in at least one embodiment, the restaurant records 254 and the menu records 256 may be data retained by a third party database separate from the system server 230. In such embodiment, the health tracking application may utilize any number of APIs to access the data in the third party databases and incorporate such information for use in the health tracking application 248, without local storage thereof and/or utilizing only temporary storage. Accordingly, it will be recognized that the description of the system server 230 of FIG. 3 is but one exemplary embodiment of a data processing system that may be utilized by the health tracking system 100.

A computer program product implementing an embodiment disclosed herein may comprise one or more computer-readable storage media storing computer instructions executable by a processor, and may provide an embodiment of a system or perform an embodiment of a method disclosed herein. Computer instructions (e.g., the health tracking application 218) may be provided by lines of code in any of various languages as will be recognized by those of ordinary skill in the art. A "non-transitory computer-readable medium" may be any type of data storage medium that may store computer instructions, including, but not limited to a memory card, ROM, RAM, write-capable memories, read-only memories, hard drives, discs, flash memory, or any of various other computer-readable medium.

Health Tracking Application

With reference now to FIGS. 4-9, representations are shown of an exemplary user interface with a restaurant search view controller provided by the health tracking application. The view controllers are made available at the system server 230 and presented to users on their health tracking devices 110 via the network 220. The view controllers include a restaurant search view controller 400 (see FIG. 4), a restaurant menu view controller 500 (see FIGS. 5-6), a restaurant food summary view controller (see FIGS. 7-8), and a food nutrition details view controller (see FIG. 9). While FIGS. 4-9 show various view controllers of the health tracking application 248 that are associated with nutrition and diet tracking features, it will be recognized that in at least some embodiments the health tracking application 248 may also include additional features, such as activity tracking, sleep tracking, or other features which may be associated with health tracking apps, as will be recognized by those of ordinary skill in the art.

Figure 4:
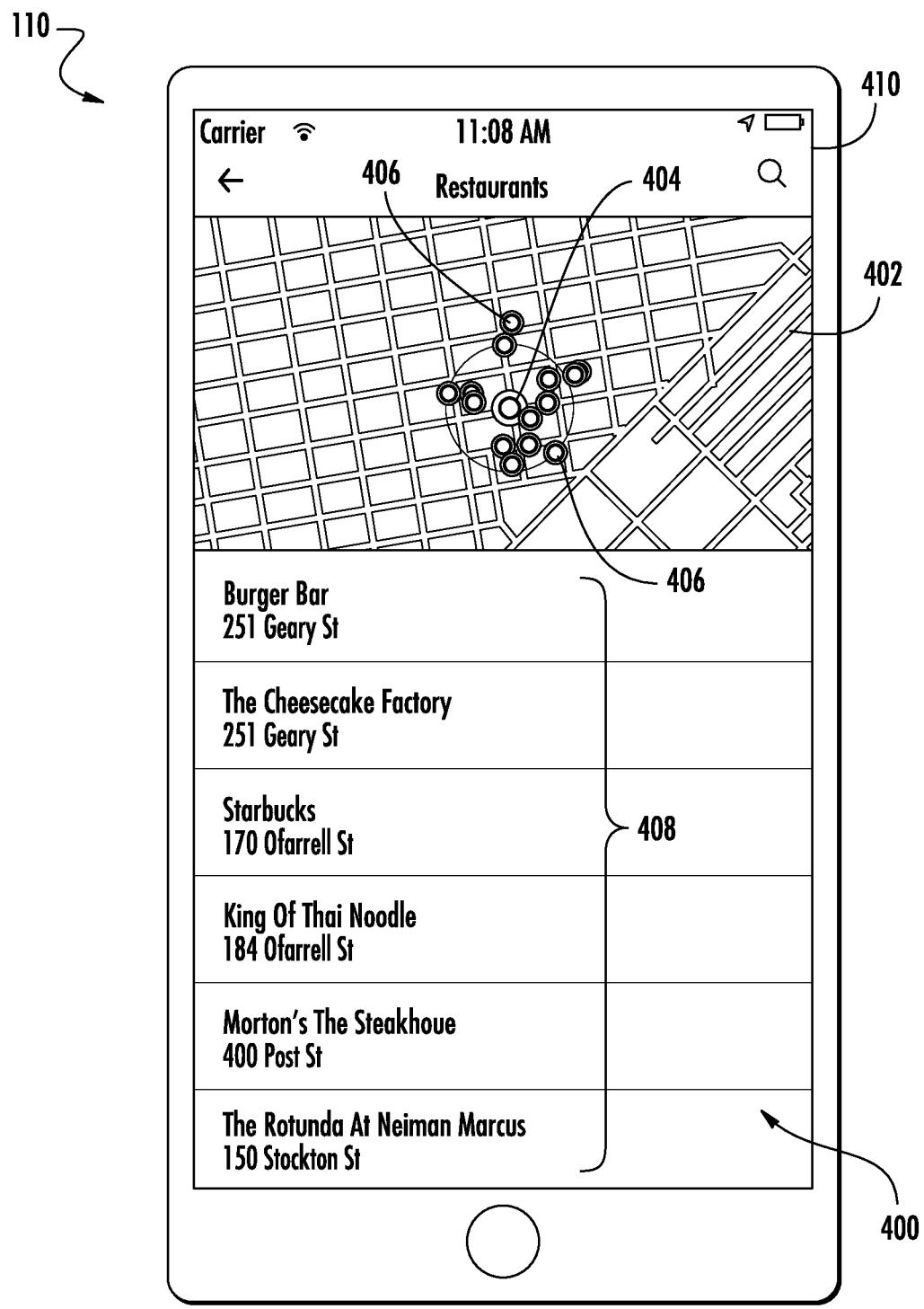
FIG. 4 is a representation of an exemplary user interface showing a restaurant search view controller provided by a health tracking application of the health tracking system and displayed on the personal electronics device of FIG. 2.

With particular reference now to FIG. 4, in at least one embodiment, the restaurant search view controller 400 is provided on the screen of a health tracking device 110. The restaurant search view controller 400 includes a map 402 showing the region where the user is currently located as determined from e.g., GPS data received from the health tracking device 110. The user's current location on the map is shown via a first designator or mark 404 and a number of nearby restaurants are shown by second designators or marks 406. The restaurants noted by marks 406 are listed individually by name and address in the table listing 408 under the map 402. In at least one embodiment, each of the second marks 406 on the map may include a reference designator (e.g., A, B, C, D, etc.), and the reference designator may be displayed next to the restaurant in the table listing to assist the user in determining the exact location of each restaurant on the map 402.

The restaurants shown on the map 402 are retrieved from the restaurant records 254 based on the location of the user and any of various additional parameters defined within the health tracking application 248. For example, the restaurants shown on the map 402 may limited to a predetermined number of restaurants closest to the user's current position (e.g., the closest ten, fifteen or twenty restaurants). Alternatively, if the user is interested in visiting a particular restaurant or a particular genre of restaurant, the user may use the search feature by selecting the search icon 410 and entering a particular restaurant name or genre of restaurant (e.g., "Starbucks" or "Coffee"). When the user makes use of the search feature, the health tracking application searches the restaurant records 254 based on the search terms entered by the user and returns a limited number of restaurants in the table listing 408 that are most closely associated with the search terms entered by the user. After reviewing the table listing 408, the user may select one of the listed restaurants to indicate he or she would like to see a menu from the selected restaurant. The selection may be made from the map 402 and/or from the table listing 408.

Figure 5:
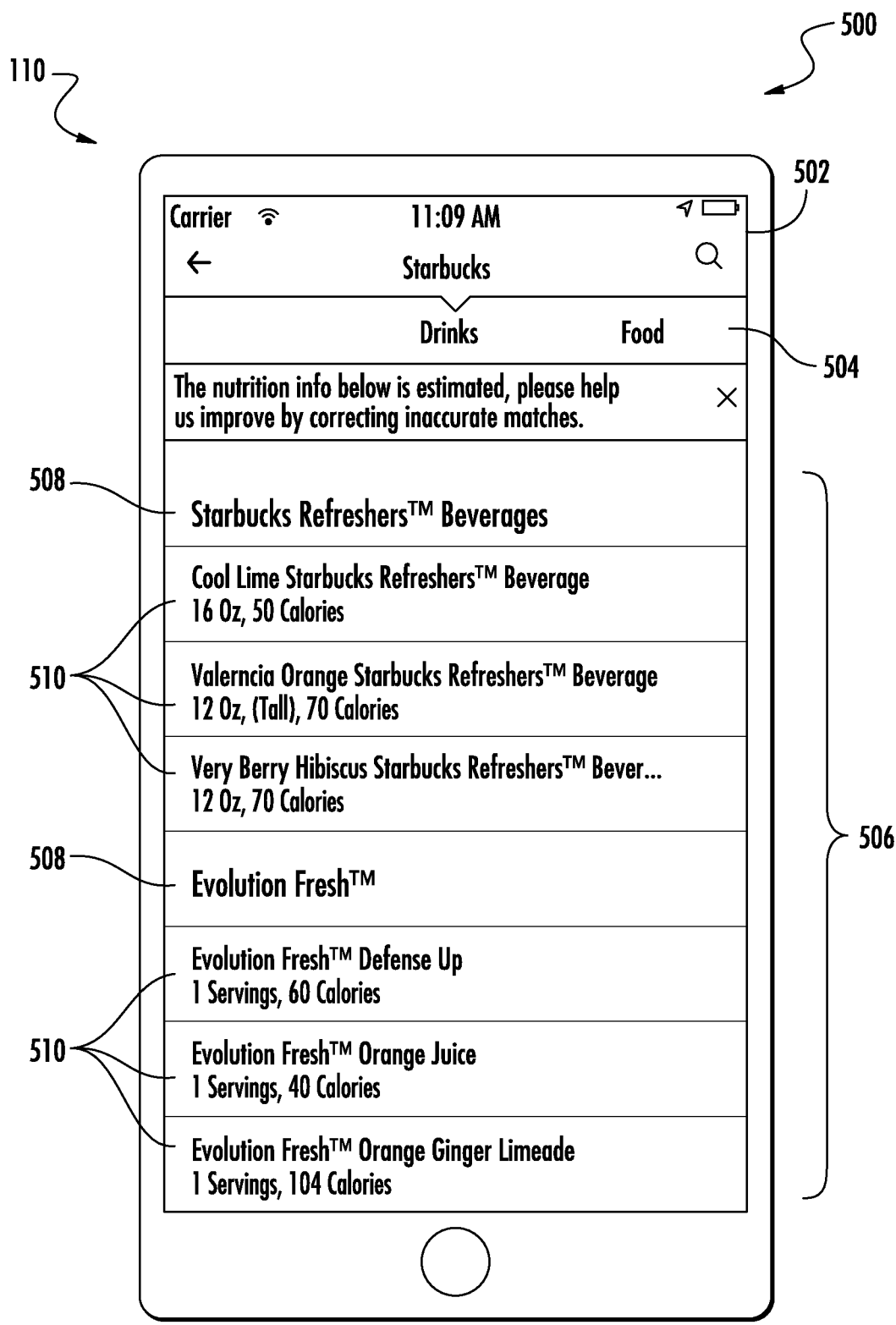
FIG. 5 is a representation of an exemplary user interface showing a restaurant menu view controller provided by the health tracking application and displayed on the personal electronics device of FIG. 2.

With reference now to FIG. 5, after selecting a restaurant from the restaurant search view controller 400, the user is presented with the restaurant menu view controller 500 on the health tracking device 110. Alternatively, if it is determined that a user is actually within the premises of a restaurant (based on GPS data) or within a predetermined proximity of a restaurant (e.g., within 10 yards), the user is automatically presented with the restaurant menu view controller without the need for the user to select any of the restaurants listed in the table listing 408. In this manner, the health tracking system 100 is advantageously configured to automatically provide the user with information which he or she is most likely interested in based on the current location of the user.

As shown in the example of FIG. 5, the user has selected "Starbucks" from the table listing 408 (or is within the premises of or a predetermined distance from the restaurant), and the restaurant menu view controller 500 is presented to the user. The restaurant menu view controller 500 includes a title block 502, a menu block 504, and a menu listing 506. The title block 502 shows the name of the restaurant (i.e., "Starbucks") that the user has selected or which the user is within the predetermined proximity of. The menu block 504 shows the various menus for the restaurant that are available for viewing. In this case, Starbucks includes a "Drinks" menu and a "Food" menu, and the user has selected the "Drinks" menu for viewing. The menu listing 506 may include various menu headings 508. In the example of FIG. 5, the menu headings 508 include, inter alia, "Starbucks Refreshers™ Beverages" and "Evolution Fresh™". The menu items 510 are listed below each menu heading 508. Each menu item includes a name and may also include a limited amount (or summary) of nutritional information for the menu item as contained within the menu records 256. In this case, each menu item 510 includes an associated serving size (e.g., 16 oz.) and an associated number of calories for the serving size (e.g., 50 calories); however other data may be presented as well.

As the user reviews the menu items 510, the health tracking application 248 searches for "matches" for each listed menu item 510 in the consumable records 258. Each "match" is an entry in the consumable records 258 that more closely resembles the menu item than other entries in the consumable records 258. Accordingly, some limited number of matches is determined for each menu item 510 presented to a user (e.g., three matches, five matches, ten matches, etc., of consumable records 258 may be matched with each menu item 510). The process of matching a number of consumable records 258 with a menu item may be determined according to any of various algorithms and methods. For example, in at least one embodiment, the process of matching may be dependent on the similarities between the names of the menu item and the consumable record. Alternatively, in at least one embodiment, the process of matching is dependent at least in part on the number of times the consumable record has been previously matched with the menu item, and/or the number of times other users have selected the consumable record when the consumable record is presented to the user in association with the menu item. In this manner, a type of crowd sourcing may be used in the matching process. In additional embodiments, other parameters such as nutritional content may be used in the matching process. Also, some weighting of parameters may be used during the matching process. For example, in considering the foregoing examples, similarity in name for the menu item and the consumable record may be most highly weighted, followed by previous matching being moderately weighted, and nutritional content similarities may be lower weighted. Accordingly, it will be recognized that the matching process may occur using any of various different algorithms and methods. In at least one embodiment, matches returned by the health tracking application 248 for a selected menu item are based at least in part on one or more of: (i) previous selected matches for the menu item, (ii) the location of the user (e.g., is the user in a particular restaurant or close to a particular restaurant), (iii) the menu selected by the user, and/or (iv) a correlation between the name of the selected menu item and the title of a consumable record.

While matching occurs as the user views the menu listing 506, the matches returned from the matching process are not presented to the user until the user actually selects one of the menu items 510 that he or she is interested in consuming or has already consumed. In this manner, the system 100 is configured to compute matches while the user scrolls through a menu, such that the system is able to present the matches to the user more quickly upon selection of a menu item. An exemplary illustration of the matches presented to the user after selecting a menu item 510 from the menu listing 506 is described in further detail below with reference to FIG. 6.

While the current example of FIG. 5 describes a situation wherein the user has selected a restaurant with a number of menus, in some situations the user may select a restaurant that does not have a menu. In these situations, the restaurant menu view controller of FIG. 5 is not presented to the user. Instead, the health tracking system 100 proceeds with matching the restaurant name to a number of consumable records, as shown in FIG. 6.

Figure 6:
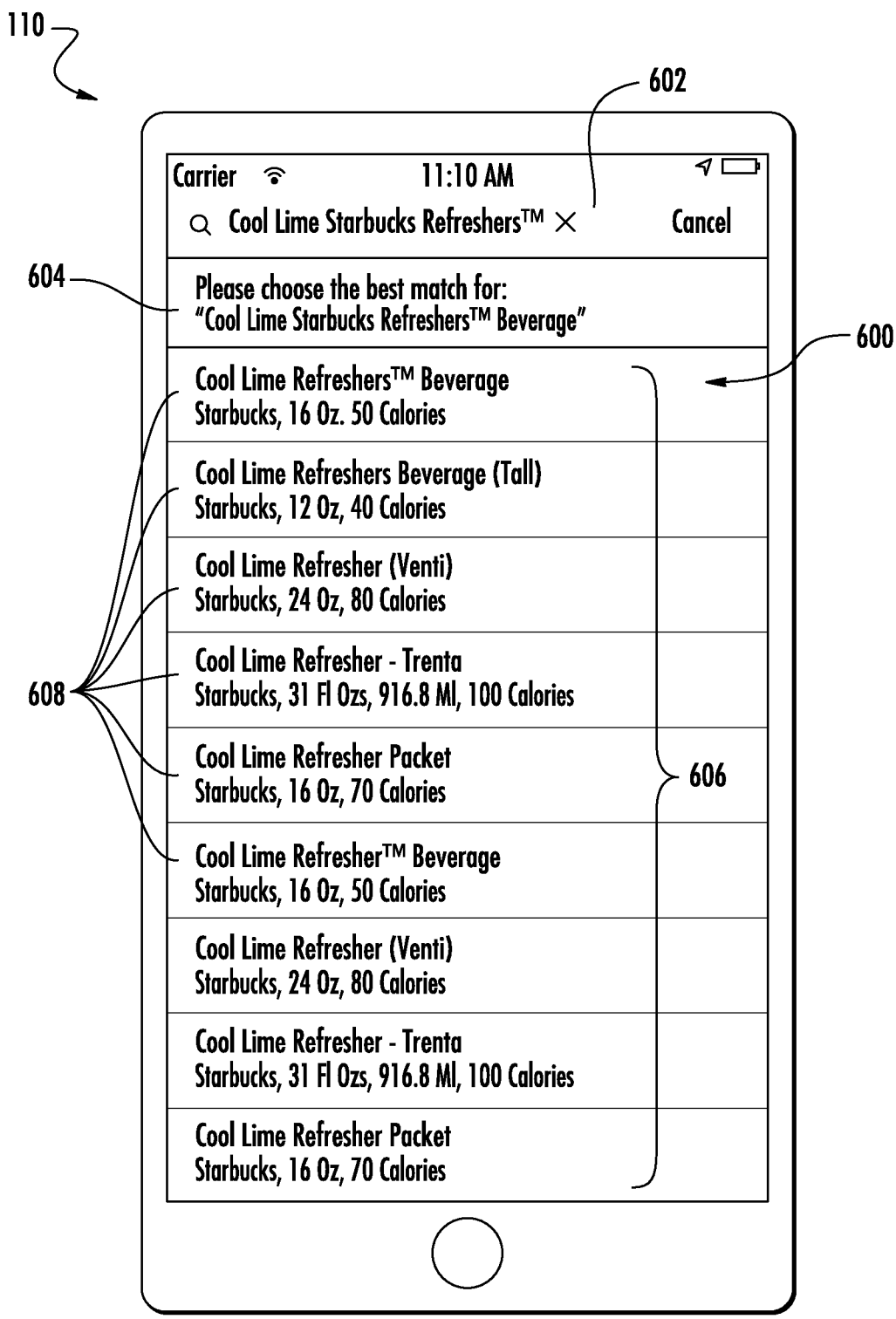
FIG. 6 is a representation of an exemplary user interface showing a match page of the restaurant search view controller provided by the health tracking application and displayed on the personal electronics device of FIG. 2.

With reference now to FIG. 6, after the user selects a menu item 510 from the restaurant menu view controller 500 (or if no menu is available, after the user selects a restaurant from the restaurant search view controller 400), the health tracking application 248 provides a match page 600. The match page 600 includes a selected menu item block 602, an instruction block 604, and a listing block 606 including a number of matches 608 from the consumable records 258. In the example of FIG. 6, the selected menu item listed in the menu item block 602 is the "Cool Lime Starbucks Refresher™" product from the Starbucks® Drink menu. The listing block 606 includes a number of matching consumable records 608 from the consumable records 258. The instruction block 604 instructs the user to choose the best match in the listing block 606 for the selected menu item. In the example of FIG. 6, each of the different consumable records includes a "Cool Lime Refreshers" beverage, but each of the different consumable records is of a different serving size. Accordingly, the user selects the match 608 in the listing block 606 that best represents the drink that the user has consumed or is interested in consuming.

Figure 7:
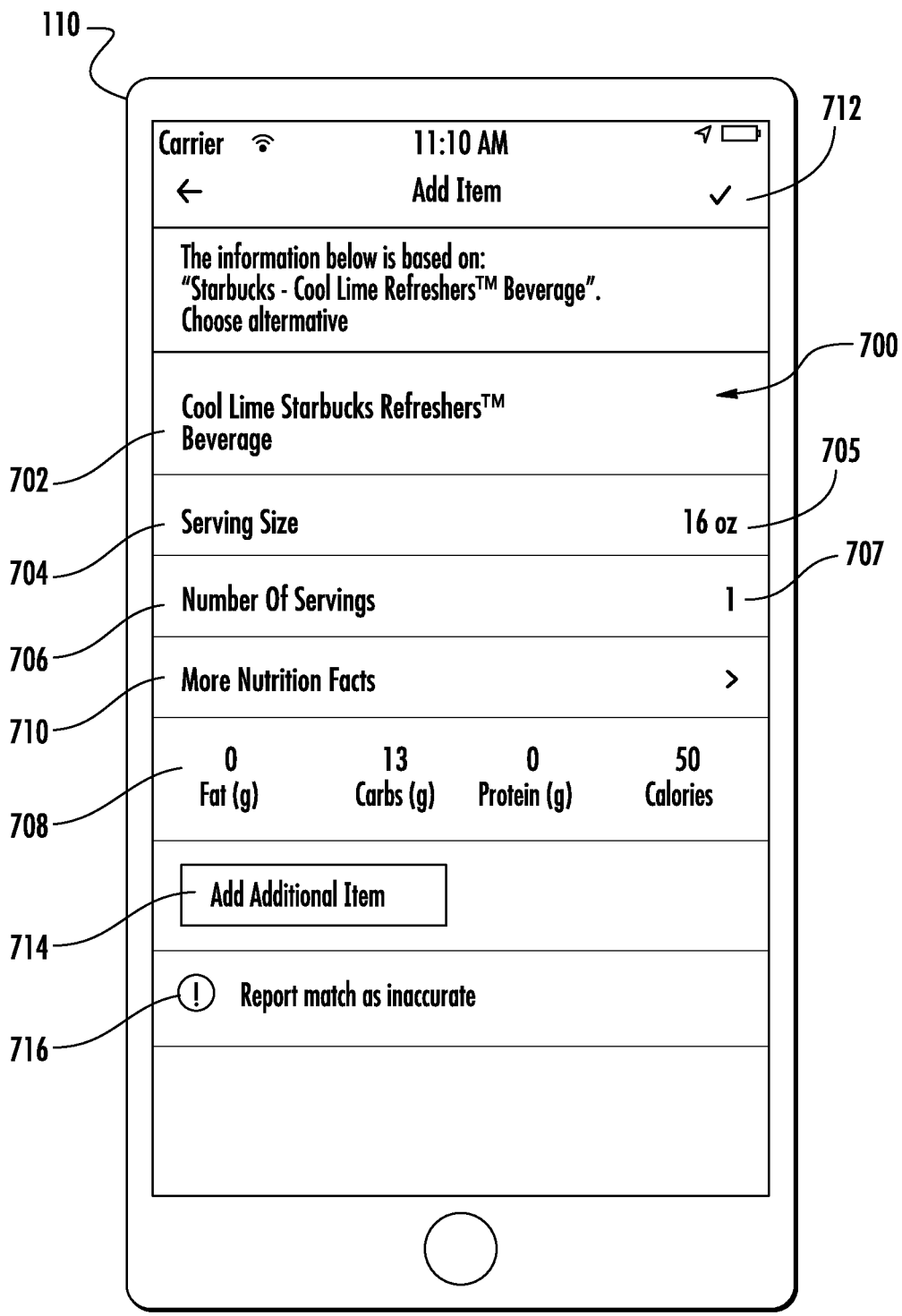
FIG. 7 is a representation of an exemplary user interface showing a food summary view controller provided by the health tracking application and displayed on the personal electronics device of FIG. 2.

With reference now to FIG. 7, after the user selects one of the matches 608, the user is presented with a food summary view controller 700. The food summary view controller 700 includes a selected match block 702, a serving size block 704, a number of servings block 706, a nutrition summary block 708, a more nutrition facts link 710, an add item option 712, an "Add Additional Item" option 714, and a "Report Match" option 716. The selected match block 702 shows the name of the consumable record that the user selected from the match page 600 (e.g., "Starbucks—Cool Lime Refresher™ Beverage"). The serving size block 704 shows the serving size of the selected match (e.g., 16 oz.). The number of servings block 706 lists the number of servings the user consumed or intends to consume (e.g., 1 serving). The nutrition summary block 708 lists a summary of nutrition facts for the selected consumable record (e.g., fat content, carbohydrates, protein, sugar, calories, etc.). If the desired nutritional data is not shown in the nutritional summary block 708, the user may select the more nutrition facts link 710, and review additional nutritional data, similar to the data shown in FIG. 8, described in further detail below.

With continuing reference to FIG. 7, if the user finds the information displayed accurate for a food or other consumable that he or she has consumed or intends to consume, the user may add the consumable record to a consumption log or diary by selecting the "Add Item" option 712. This will cause the health tracking application 248 to add the consumable record to the user's food consumed for the day. On the other hand, if the user wishes to modify the consumable record, the user may do so in the food summary view controller 700. For example, in the embodiment of FIG. 7, the serving size block 704 and number of servings 706 are both editable by the user. Thus, if the user consumed a 20 oz. serving of the beverage, the user simply taps the "16 oz" entry 705 in the serving size block 704 of FIG. 7, and a text box appears allowing the user to change the serving size from "16 oz." to "20 oz". Similarly, if the user consumed two servings instead of one of the listed beverage, the user simply taps the "1" entry 707 in the number of servings block 706, and a text box appears allowing the user to change the number of servings consumed from "1" to "2".

After amending the data for the listed consumable by changing either the entry in the serving size block 704 or the number of servings block 706, the user may enter the amended data as a new item in the consumable records 258 by selecting the "Add Additional Item" option 714. When this option 714 is selected, the consumable records 258 is updated to include the amended consumable record as a new consumable record. As an example, if the serving size of FIG. 7 is amended from "16 oz" to "20 oz", the user may select the "Add Additional Item" option 714 to add the entry as a new consumable record within the consumable records 258. As a result, the consumable records 258 will include at least two records with the "Cool Lime Starbucks Refreshers™ Beverage" name, one being a 16 oz version and the other being the new 20 oz version.

In addition to the above, if the user believes that a particular consumable record presented to the user on the food summary view controller 700 is inaccurate for some reason, the user may choose the "Report Match as Inaccurate" option 716. By selecting this option, the user can submit an entry requesting the system administrator to review a particular record in the consumable records as being inaccurate. For example, if Starbucks does not offer a 16 oz version of the "Cool Lime Refreshers™ Beverage", the user may select the "Report Match as Inaccurate" option 716 and make a note to the system administrator requesting the consumable records to be amended for the reason provided.

Figure 8:
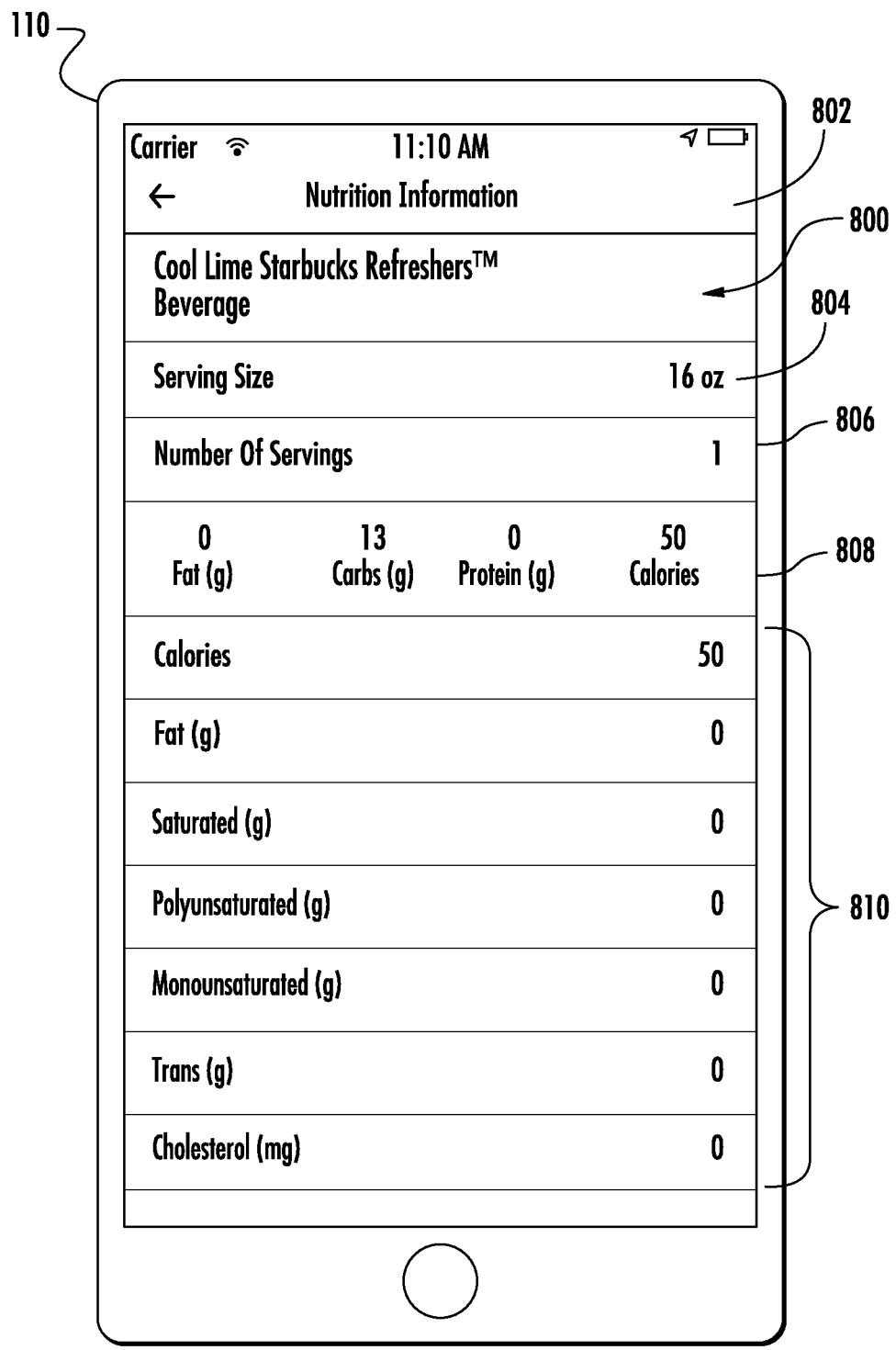
FIG. 8 is a representation of an exemplary user interface showing a restaurant nutrition view controller provided by the health tracking application and displayed on the personal electronics device of FIG. 2.

As noted above, if the user wishes to obtain even more nutritional information for the selected consumable record, the user may select the more nutrition facts link 710, as shown in FIG. 7. If the user selects this link 710, the user is presented with even more nutritional facts for the selected consumable record in a restaurant nutrition details view controller. For example, FIG. 8 shows a restaurant nutrition view controller 800 presented to the user following selection of the more nutrition facts link 710 of FIG. 7. The restaurant nutrition view controller 800 includes a selected match block 802, a serving size block 804, a number of servings block 806, a nutrition summary block 808, and an additional nutrition facts table 810. The selected match block 802, the serving size block 804, the number of servings block 806, and the selected nutrition summary block 808 function in the same way as the associated blocks 702, 704, 706 and 708 operate, as described above. However the additional nutrition facts table 810 provides additional nutrition information that is not provided in the nutrition summary block 808. This additional nutritional information may include any of various types of more specific nutritional information such as vitamin content, fat content, cholesterol content, sugar content, fiber content, protein content, or any of various additional types of nutritional information as will be recognized by those of ordinary skill in the art.

In at least one embodiment, each consumable record 258 may be provided as either a "food item" or a "recipe". A "food item" is defined in a manner such that it cannot be parsed into a list of ingredients (e.g., "chicken sandwich," without a detailed list of the ingredients on the chicken sandwich). While a "food item" may have a serving size (e.g., one, two, etc.), the user does not have the ability to edit the food to remove any particular part of the food item (e.g., the bread cannot be removed from the chicken sandwich) or add anything to the food item. On the other hand, a "recipe" is defined in a manner such that it may be parsed into a list of ingredients (e.g., bread, chicken, lettuce, tomato, mayo, mustard, peppers, etc.). Accordingly, a recipe is editable by the user to remove any particular ingredient (e.g., remove bread from the chicken sandwich) or add a particular ingredient (e.g., add mayonnaise to the chicken sandwich). Therefore, "foods" may be considered "unitary" (or "homogeneous") in nature, while "recipes" are "multi-component" (or "heterogeneous") in nature.

Figure 9:
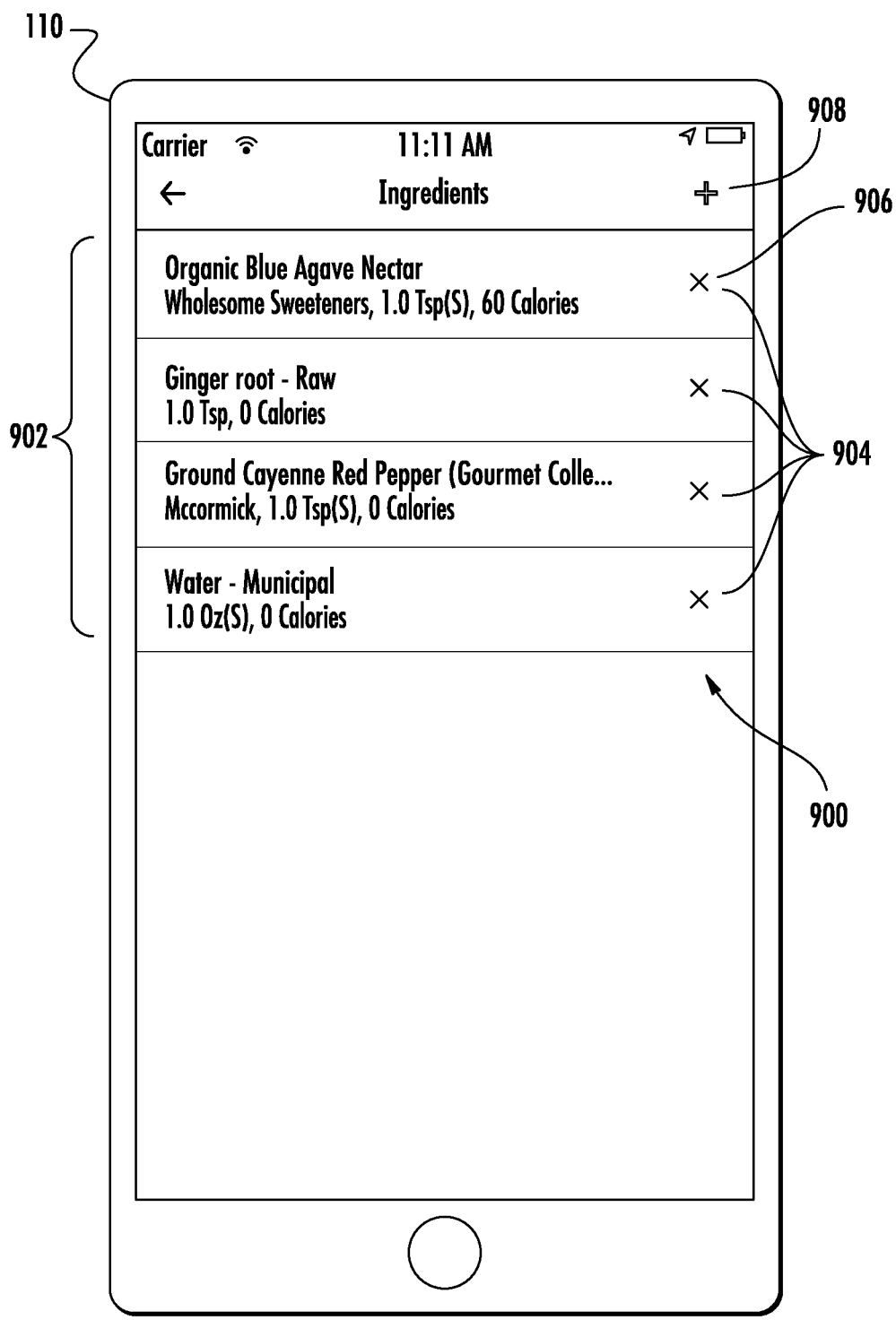
FIG. 9 is a representation of an exemplary user interface showing a recipe view controller provided by the health tracking application and displayed on the personal electronics device of FIG. 2.

FIG. 9 shows an exemplary embodiment of a recipe ingredients view controller 900 for a consumable record. The recipe ingredients view controller 900 may be displayed when the user selects the more nutrition facts link 710 from a provided link for the consumable record (e.g., the food summary view controller 700 of FIG. 7) and the consumable item is a recipe with multiple ingredients instead of a unitary food item. In the recipe ingredients view controller 900, the user is presented with an ingredients list 902 comprising a number of ingredients 904 that are combined to make the recipe. Nutritional information for each ingredient 904 is provided below the ingredient. Additionally, the user may select the ingredient 904 in the ingredients list 902 to obtain additional nutritional information about the ingredient (similar to the nutritional information view controller 800 of FIG. 8). Furthermore, the user may choose to remove any ingredient in the list or add ingredients. In particular, if the user selects the "x" option 906 in the rightmost column of the ingredients list, the ingredient in that row will be removed from the recipe. Alternatively, if the user selects the "+" option 908 in the header, additional ingredients may be added to the recipe. In this manner, if the consumable record is a recipe for a "chicken sandwich", the user may easily add or remove ingredients from the chicken sandwich. For example, if the recipe includes "mustard" but not "mayonnaise", the user may remove the "mustard" ingredient and add "mayonnaise" to arrive at more complete nutritional data for the consumable that he or she has consumed.

Method of Providing Nutritional Data for a User

Figure 10:
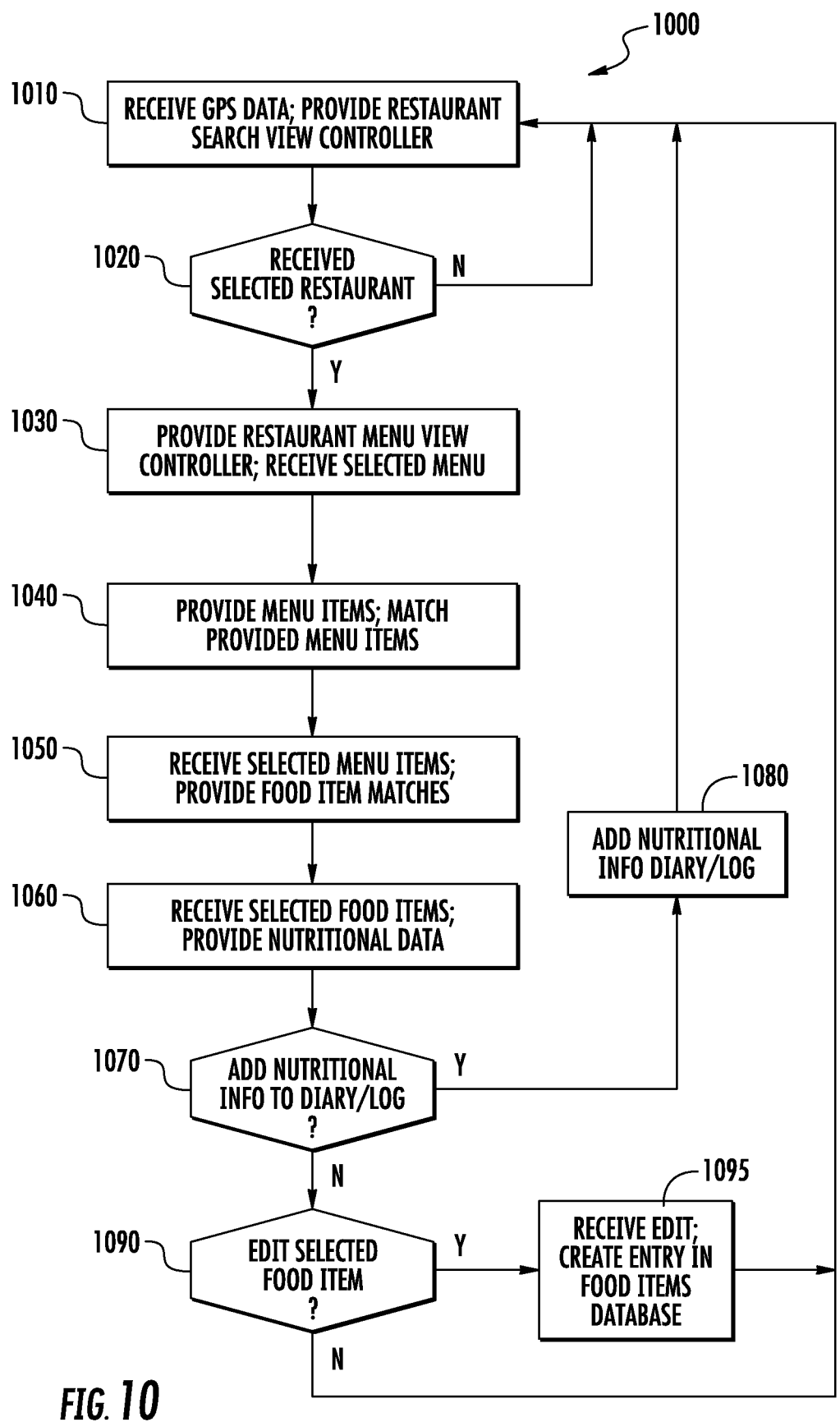
FIG. 10 is a logical flow diagram illustrating a method of providing nutritional data for a user using the health tracking system of FIG. 1.

With reference now to FIG. 10, a method 1000 of providing nutritional data for a user using the health tracking application 248 is shown. The method begins with step 1010 wherein the health tracking application 248 receives GPS data from the health tracking device 110 of the user. The health tracking application 248 then provides the restaurant search view controller to the user (e.g., the exemplary restaurant search view controller 400 of FIG. 4). The user then reviews the restaurants displayed on his or her health tracking device 110 and selects one of the restaurants. As noted previously, the restaurants displayed are generally based on the location of the user but may also be based on a search term entered by the user (e.g., a genre of restaurant or a specific restaurant name). In at least one embodiment, the restaurant may deemed to be selected by virtue of the user's location within the premises of the restaurant or in proximity to the restaurant.

In step 1020 of FIG. 10, the health tracking application 248 determines whether a restaurant has been selected by the user. If no restaurant has been selected by the user, the health tracking application 248 continues processing at step 1010 and receives GPS data from the user. However, if a restaurant is selected by the user, the health tracking application 248 continues processing at step 1030.

At step 1030 of FIG. 10, the health tracking application 248 provides a restaurant menu view controller for the user (e.g., the exemplary restaurant menu view controller 500 of FIG. 5). The restaurant menu view controller allows the user to select a menu to view, wherein the viewed menu is associated with the restaurant. After the user selects one of the menus or in the instance no menu is provided, the health tracking application 248 continues processing at step 1040.

At step 1040, a number of associated menu items from the selected menu are provided to the user such that the user may view the menu items on his or her personal electronics device 110. As the user reviews the menu items, the health tracking application 248 determines a number of matches for each menu item from the consumable records 258. The matches are retained by the health tracking application 248, but are not displayed for the user until the user selects one of the menu items. In at least one alternative embodiment, the health tracking application 248 does not determine matches for the menu items until one of the menu items is selected by the user. After the user reviews the menu items on his or her health tracking device 110, the user then selects one menu item that is closest to the menu item that he or she is interested in consuming (or has already consumed).

At step 1050, the health tracking application 248 receives a selected menu item from the user and provides the determined matches for the selected menu item for the user to view on his or her health tracking device 110 (e.g., exemplary matches for a selected menu item are shown in the match page 600 of FIG. 6). The user then selects one of these matches as the consumable record that best represents the food that he or she intends to consume or has consumed. The health tracking application 248 continues processing at step 1060 and receives the selected match. The user is then presented with additional nutritional data about the selected match.

In step 1070, the user is given the option of adding the nutritional data for the selected match to his or her consumption diary/log for the day. Accordingly, if the user has consumed (or intends to consume) the selected match, and the nutritional data for the selected match appears to be appropriate for the food consumed, the user may simply make a selection to add this nutritional data to his or her consumption diary/log for the day (e.g., in the embodiment of FIG. 7, the user may select the "Add Item" option 712). If the user selects to add the nutritional data to the consumption diary/log, the health tracking application 248 continues processing at step 1080, and the nutritional information is added to the user's personal consumption diary/log. On the other hand, if the user does not wish to add the nutritional data for the selected consumable record to the user's personal consumption diary/log, the user may instead indicate that he or she wishes to edit the selected foot item at step 1090.

At step 1090 the health tracking application 248 determines whether the user wishes to edit the selected match (e.g., if the user has amended to serving size entry 705 or the number of servings entry 707 for the selected match and has selected the "add additional item" option 714). If the user has indicated that the user wishes to edit the selected match, the health tracking application 248 continues processing by moving to step 1095 and receiving the edit and creating a new entry in the consumable records 258 for the edited consumable record. Any of various edits are possible. For example, in the embodiment of FIG. 7, a change to the serving size entry 705 or the number of servings entry 707 may result in the creation of a new consumable record. However, changes in any other nutritional data may also be entered as a new consumable record, as discussed above when ingredients maybe added or removed from a recipe. If the user does not indicate that he or she is interested in adding or editing the selected consumable record (i.e., in steps 1070 or 1090) after a given period of time, the user may be return to any previous view controller, or the health tracking application 248 may return the user to the restaurant search view controller, as noted in the exemplary embodiment of FIG. 10.

As an example of the above steps 1010-1095, consider the example of FIGS. 4-9 where the user is presented with a list of restaurants in the restaurant search view controller 400 of FIG. 4 and selects to view the menu of the nearby "Starbucks®" restaurant. In FIG. 5, the user is presented with the Drinks menu from the "Starbucks" restaurant. The user then selects the "Cool Lime Starbucks Refreshers™ Beverage" menu item from the list of menu items 510 in FIG. 5. In association with selection of this menu item, the health tracking application 248 searches the consumable records 258 and retrieves a list of possible consumable record matches. This list is presented on a match screen 600 of the restaurant menu view controller as shown in FIG. 6. The user then reviews these consumable record matches (shown in FIG. 6) to determine which of these matches most closely resembles what the user is interested in consuming (or has already consumed) from the restaurant. In this example, the user is interested in a 16 oz. Cool Lime Refreshers Beverage. The user is not interested in the 12 oz. ("Tall") option, the 24 oz. ("Venti") option, or the "Packet" option. Accordingly, the user selects the first match presented on the match screen of FIG. 6 (i.e., the 16 oz. "Cool Lime Refreshers Beverage"). The user is then presented with additional nutritional data in the restaurant food summary view controller 700 in the screen of FIG. 7. This screen provides the user with information about the selected match, including serving size, fat, carbohydrate, protein, calorie, or other information. If the user would like to post the selected consumable record to his or her consumption diary/log for the day, the user simply selects the "Add Item" option 712 to enter this consumable record into the consumption diary/log. If the user wishes to amend the information for the selected consumable record and create a new item in the database, the user selects the "Add Additional Item" option 714, which allows the user to create a new consumable record in the consumable records based on the selected consumable record. Alternatively (or additionally), if any of the information about the consumable record is incorrect, the user may "Report the match as inaccurate" by selecting option 716. If the user wishes to view even more information about the consumable record before adding the consumable record to his or her consumption diary/log, the user selects the "More Nutrition Facts" link 710 and is presented with the restaurant food nutrition details view controller of FIG. 8. The restaurant food nutrition details view controller provides the user with additional data about the selected consumable record match. For example, as shown in FIG. 8, further information about fat, cholesterol, and other nutrition details about the exemplary 16 oz. "Cool Lime Starbucks Refreshers Beverage" may be obtained on this page. Further nutrition details about the consumable associated with the consumable record may be presented to the user when the user scrolls down the page. Alternatively, if the matched consumable record is a "recipe" (instead of a "food"), the user may be presented with an additional selection that takes the user to a page similar to the restaurant recipe ingredients view controller 900 of FIG. 9.

Menu Filtering

With reference now to FIGS. 11-19, representations are shown of an exemplary user interface with a menu filter view controller provided by the health tracking application. The view controllers are made available at the system server 230 and presented to users on their health tracking devices 110 via the network 220. The view controllers include a restaurant menu view controller 1100 (see FIGS. 11 and 18-19) and a menu filter view controller 1200 (see FIGS. 12-17).

Figure 11:
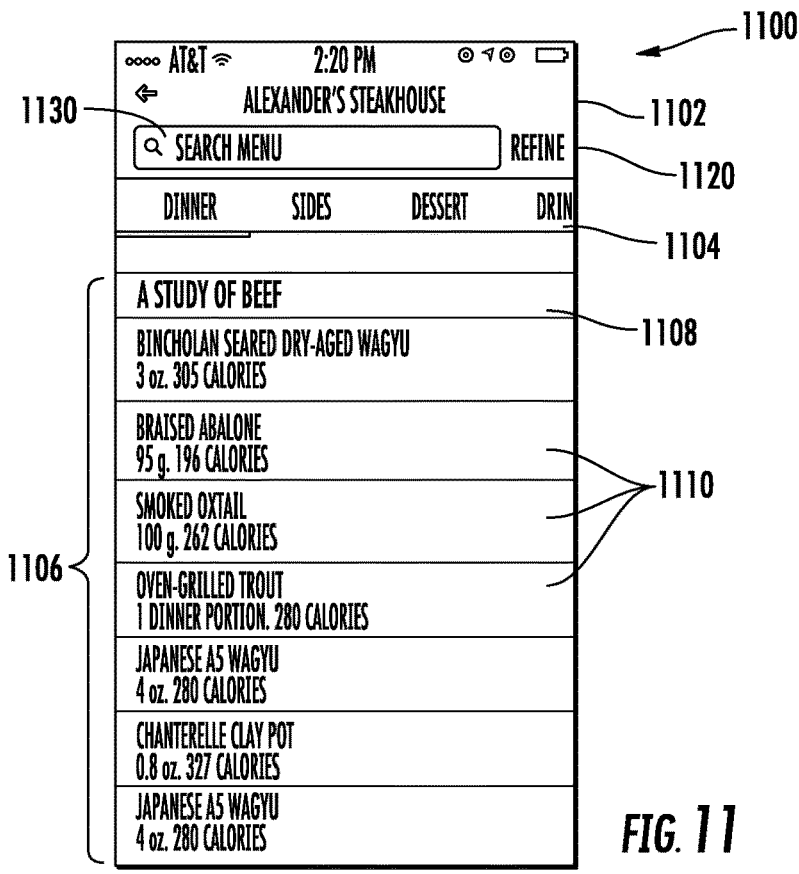
FIG. 11 is a representation of an exemplary user interface showing an alternative embodiment of a restaurant menu view controller provided by the health tracking application and displayed on the personal electronics device of FIG. 2.

With particular reference now to FIG. 11, an embodiment of a restaurant menu view controller 1100 is shown. The restaurant menu view controller 1100 is similar to the restaurant menu view controller 500 described previously in association with FIG. 5, and includes a title block 1102, a menu block 1104, and a menu listing 1106. Additionally, in the embodiment of FIG. 11, the restaurant menu view controller 1100 includes a menu filter option 1120 and a menu search option 1130.

The title block 1102 shows the name of the restaurant (i.e., "Alexander's Steakhouse") that the user has selected or which the user is within the predetermined proximity of. In at least one embodiment, the restaurant menu view controller 1100 is presented to the user after selecting a restaurant from a restaurant search view controller (e.g., the restaurant search view controller 400 of FIG. 4). Alternatively, if it is determined that a user is actually within the premises of a restaurant (based on GPS data) or within a predetermined proximity of a restaurant (e.g., within 10 yards), the user may be automatically presented with the restaurant menu view controller 1100 without the need for the user to select any of the restaurants listed in the restaurant search view controller. In this manner, the health tracking system 100 is advantageously configured to automatically provide the user with information which he or she is most likely interested in based on the current location of the user.

With continued reference to FIG. 11, the user has selected "Alexander's Steakhouse," and the restaurant name appears in the title block 1102. The menu block 1104 shows the various menus for Alexander's Steakhouse that are available for viewing. In this case, Alexander's Steakhouse includes a "Dinner" menu, a "Sides" menu, a "Dessert" menu, and a "Drinks" menu. Only a portion of the "Drinks" menu option is provided to show the user that additional menu options are available by scrolling across menu block 1104 (e.g., moving the listed menu options to the left) such that additional menu options to the right of the "Drinks" menu are shown in the title block 1102.

The menu listing 1106 shows menu data associated with the selected menu from the menu block 1104. The menu listing may include various menu headings 1108 as well as associated menu items 1110. In the example of FIG. 11, the menu headings 1108 include the "A Study of Beef" menu heading 1108. Additional menu headings 1108 may be viewed by scrolling down the menu listing 1106 (e.g., by moving the menu listing 1106 upward).

The menu items 1110 are listed below each menu heading 1108. Each menu item 1110 includes a name and may also include a limited amount (or summary) of nutritional information for the menu item as contained within the menu records 256. In FIG. 11, the names of the dinner menu items include, inter alia, "Binchotan Seared Dry-Aged Wagyu," "Braised Abalone," "Smoked Oxtail," and "Oven-Grilled Trout". The summarized nutritional information associated with each menu item 1110 may include an associated serving size (e.g., 3 oz., 95 grams, etc.) and an associated number of calories for the serving size (e.g., 305 calories, 196 calories, etc.). This nutritional information associated with each menu item 1110 is typically obtained from a menu record 256 that is provided by the restaurant or other trusted source that is associated with the menu. However, if any nutritional information is missing or incomplete from such menu record, the nutritional information may be obtained by one or more consumable records, such as a consumable record that has been selected most frequently in association with the menu item.

As the user scans the menu items 1110, the health tracking application 248 searches for "matches" for each listed menu item 1110 in the consumable records 258. Each "match" is an entry in the consumable records 258 that more closely resembles the menu item than other entries in the consumable records 258. As described previously with reference to the embodiment of the menu view controller of FIG. 5, matches returned by the health tracking application 248 for a selected menu item are based at least in part on one or more of: (i) previous selected matches for the menu item, (ii) the location of the user (e.g., is the user in a particular restaurant or close to a particular restaurant), (iii) the menu selected by the user, and/or (iv) a correlation between the name of the selected menu item and the title of a consumable record. While matching occurs as the user views the menu listing 1106, the matches returned from the matching process are not presented to the user until the user actually selects one of the menu items 1110 that he or she is interested in purchasing or has already purchased. In this manner, the system 100 is configured to compute matches while the user scrolls through a menu, such that the system is able to present the matches to the user more quickly upon selection of a menu item. After selecting a menu item 1110 from the menu listing 1106, the user is presented with a match page, similar to that described previously with reference to FIG. 6.

The restaurant menu view controller of FIG. 11 also provides the user with the functionality of re-ordering or otherwise limiting the menu items displayed to the user via the menu filter option 1120. This menu filter option 1120 is useful if the restaurant menu lists a number of menu items that the user is not interested for various reasons. For example, a user may not be interested in a significant number of menu items because the consumables associated with such menu item include an excessive number of calories that are not on the user's diet or will cause the user to fail to meet his or her goals for the day.

Figure 12:
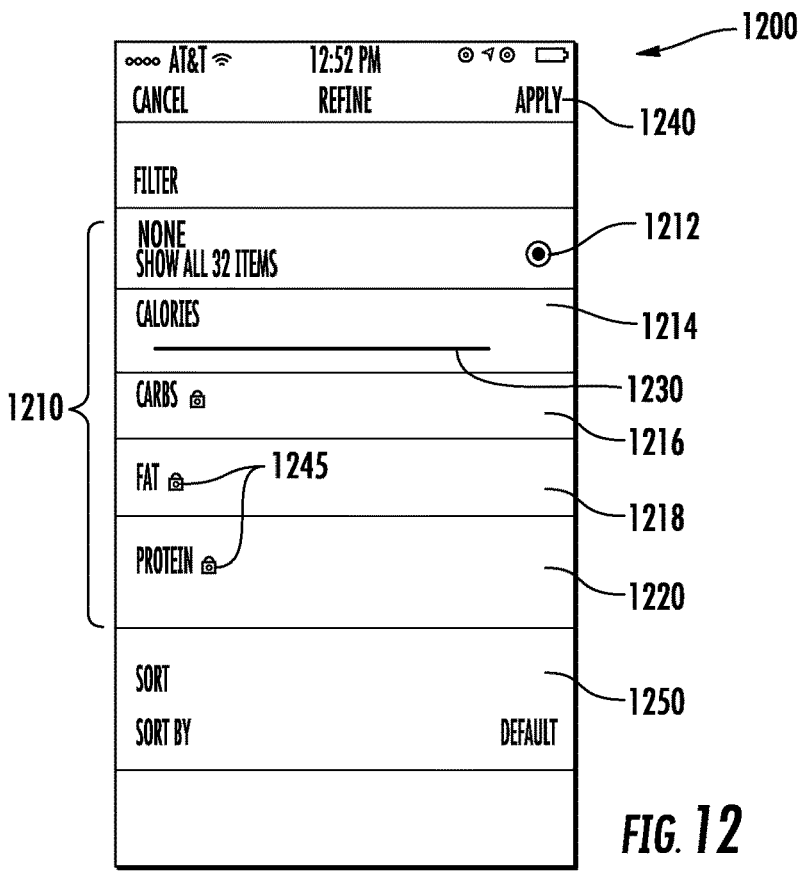
FIG. 12 is a representation of an exemplary user interface showing a filter page of the restaurant search view controller of FIG. 11 with no filter selected.

After the user selects the menu filter option 1120 of FIG. 11, the user is presented with a filter page 1200, such as that shown in FIG. 12. The filter page 1200, allows the user to apply a filter to the menu items 1110 in the menu listing 1106 such that menu items that fall outside of defined parameters are removed from the menu listing 1106 presented to the user. In particular, the filter page 1200 allows the user to filter menu items 1110 that fall outside of defined calorie ranges or macronutrient ranges such as carbohydrates, fat, protein, etc. Accordingly, the filter page 1200 includes a plurality of filter options 1210 that allow the user to apply one or more filter metrics to the menu listing 1106 that was previously presented to the user. The filter metric may be defined in any of various manners, such as a specific value, or a range of values for the menu items. In the embodiment of FIG. 12, at least one range of values is defined by the user using and at least one of a plurality of associated range bars 1230. The range bars 1230 allow the user to define an upper and lower limit of the associated menu item parameter. In the embodiment of FIG. 12, the filter options 1210 include a "none" filter option presented in block 1212, a "calories" filter option presented in block 1214, a "carbohydrates" option presented in block 1216, a "fat" filter option presented in block 1218, and a "protein" filter option presented in block 1220. In the embodiment of FIG. 12, the user has selected the "none" filter option in block 1212 (as indicated by the highlighted circle in the "none" option block 1212). As shown in the block 1212, selection of the "none" filter option will result in all 32 menu items 1110 from the associated menu being presented to the user on the restaurant menu view controller 1100 of FIG. 11. It is further appreciated that other filters may be applied and utilized similarly to those discussed herein, for example, filters based on amount of sugar, cholesterol, salt, vitamins, etc.

Figure 13:
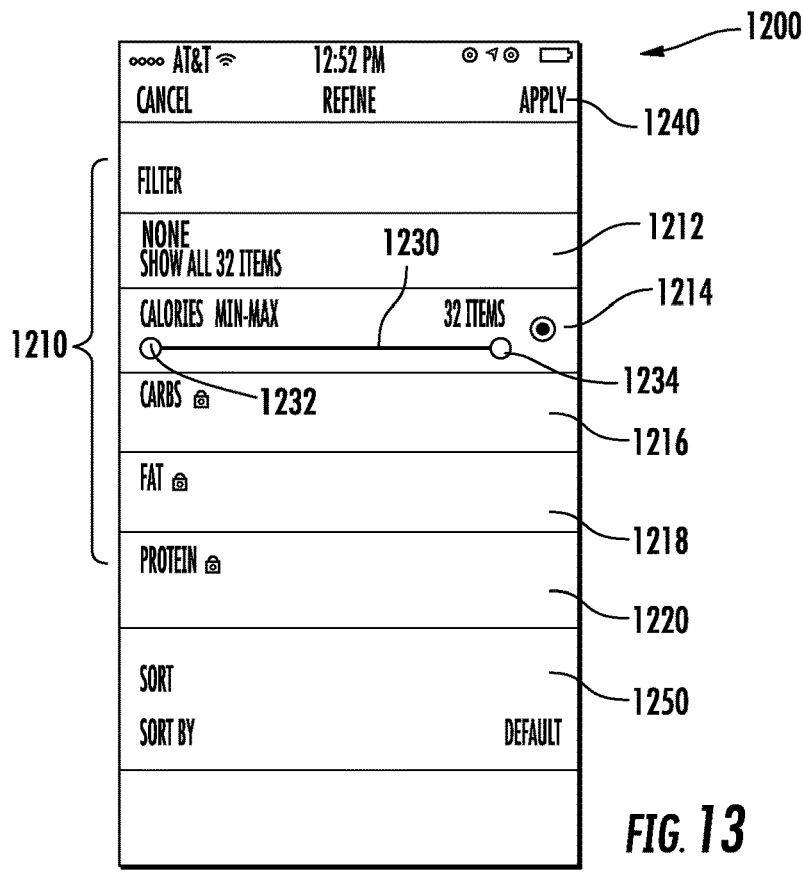
FIG. 13 is a representation of an exemplary user interface showing the filter page of FIG. 12 with a calorie filter selected.

With reference now to FIG. 13, the user has selected the "calories" filter option presented in block 1214 of the filter page 1200. Accordingly, the circle in block 1214 associated with the "calories" filter option is highlighted, and the circle in block indicating no filters are applied 1212 is no longer highlighted (as previously shown in FIG. 12). Block 1214 includes a range bar 1230 including a lower end slider 1232 and an upper end slider 1234 that allows the user to define a calorie range for menu items to be shown to the user. In FIG. 13, the user has yet to restrict the calories to a particular range using the bar 1230. Accordingly, the menu block 1214 indicates that all 32 menu items from the associated menu will be presented to the user on the restaurant menu view controller 1100. As the user slides the calorie bar 1230, more or fewer menu items are included in the resultant list.

Figure 14:
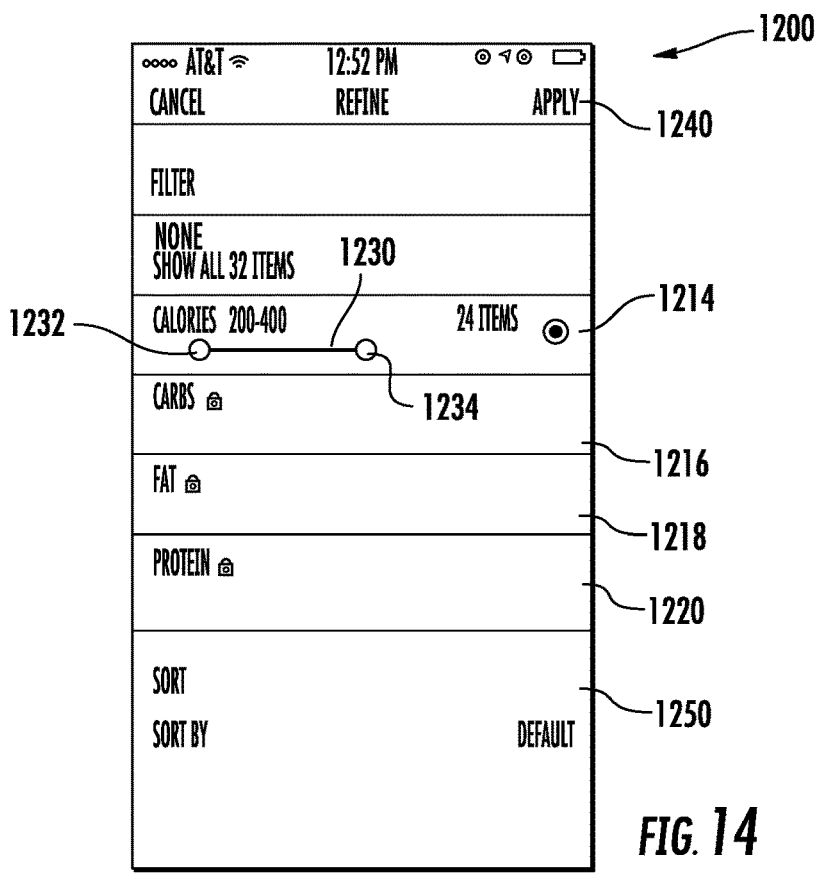
FIG. 14 is a representation of an exemplary user interface showing the filter page of FIG. 13 with the calorie filter defined within a range of calories.

In FIG. 14, the user has defined calorie range using the range bar 1230 of the filter page 1200. In particular, the user has moved the lower end slider 1232 of the range bar 1230 to the right to indicate a lower calorie limit (or threshold) of 200 calories, and has moved the upper end slider 1234 of the range bar 1230 to the left to indicate an upper calorie limit (or threshold) of 400 calories. The user may adjust this calorie range as desired. To reduce the lower calorie limit, the user simply moves the lower end slider 1232 to the left along the range bar 1230; to increase the lower calorie limit, the user moves the lower end slider 1232 to the right along the range bar 1230. Similarly, to reduce the upper calorie limit, the user simply moves the upper end slider 1234 to the left along the range bar 1230; to increase the upper calorie limit, the user moves the upper end slider 1234 to the right along the range bar 1230. In the embodiment of FIG. 14, the user has defined a calorie range between 200 and 400 calories, as shown in the calorie filter block 1214. The calorie filter block 1214 also indicates that 24 menu items are within the defined calorie range.

With continued reference to FIG. 14, in addition to the calorie filter block 1214, the filter options 1210 further include the "carbohydrates" filter block 1216, the "fat" filter block 1218, and the "protein" filter block 1220. Each of these blocks 1216, 1218 and 1220 includes an associated range bar 1230 including a lower end slider 1232 and an upper end slider 1234 that allows the user to define a macronutrient range for menu items to be shown to the user. In the embodiment of FIGS. 12-14, the user is locked out from selecting any of the macronutrient filter options because the user has only subscribed to a basic service level. Accordingly, a lock 1245 appears next to each of the macronutrient filter blocks 1216, 1218 and 1220. However, if the user upgrades to a premium level of service, the locks 1245 are removed, and the user may define macronutrient filter parameters, as explained in further detail below with reference to FIG. 18.

Figure 15:
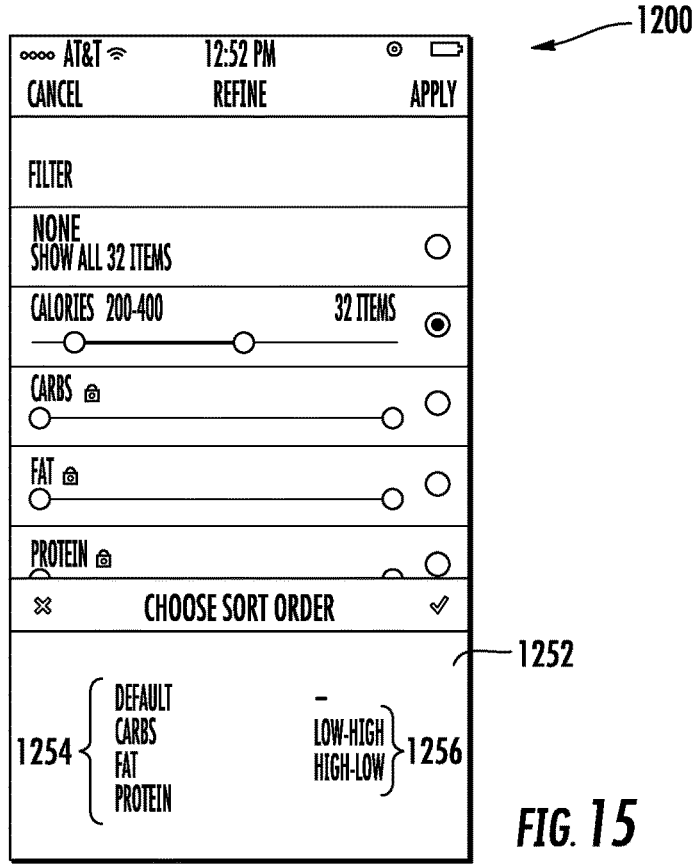
FIG. 15 is a representation of an exemplary user interface showing the filter page of FIG. 14 with a sort option selected.
Figure 16:
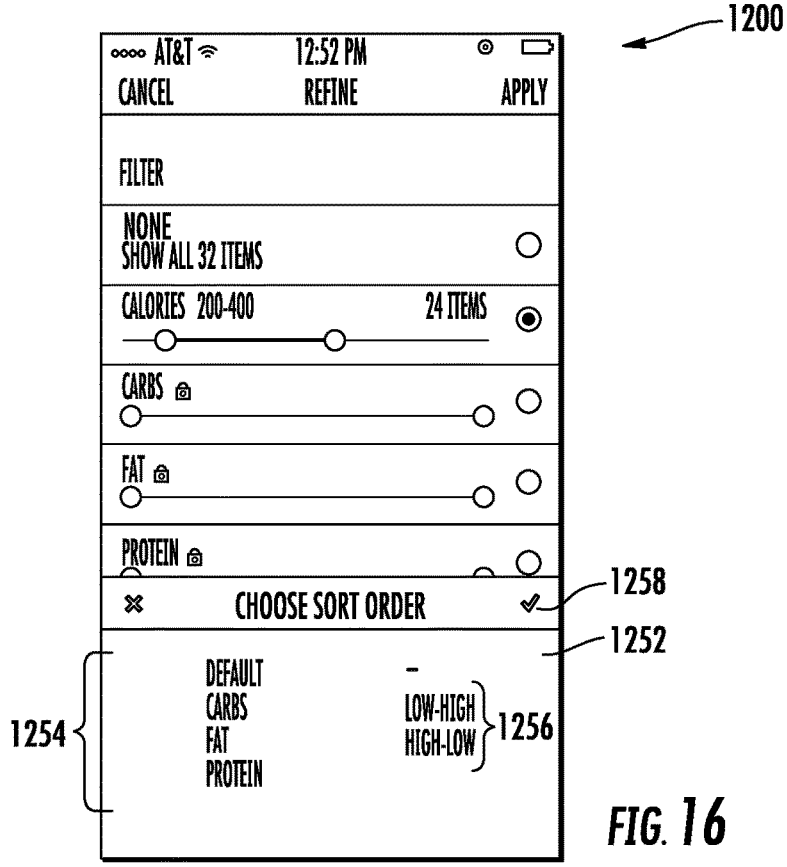
FIG. 16 is a representation of an exemplary user interface showing the filter page of FIG. 15 with a sort order defined.

With continued reference to FIGS. 15-16, the filter page 1200 further includes a sort order option at block 1250. When the user selects this block 1250, the user is presented with a sort sub-page 1252 (while may also be referred to as a pop-up menu) on the filter page 1200, as shown in FIG. 15. The sort sub-page 1252 includes a number of sort options, including first sort options 1254 and second sort options 1256 that allow the user to define a sort order for menu items to be presented on the restaurant menu view controller 1100.

In the embodiment of FIG. 15, the first sort options 1254 include a "Default" option, a "Carbs" option, a "Fat" option, and a "Protein" option. The second sort options 1256 include a "Low-high" option, and a "High-Low" option. The "Default" option is highlighted in FIG. 15, indicating that menu items displayed on the restaurant menu view controller 1100 will be ordered according to some "Default" (e.g., a low-high order for the associated defined range, such as "calories" as defined in FIG. 14). The "Carbs" option allows the user to select the menu items displayed on the restaurant menu view controller 1100 according to carbohydrate value, with the order arranged by the selected second sort options 1256 of either "Low-high" or "High-low." Similarly, the "Fat" option and the "Protein" option allow the user to select the menu items displayed on the restaurant menu view controller 1100 according to fat or protein value, respectively, with the order arranged by the selected second sort options 1256 of either "Low-high" or "High-low." In FIG. 16, the "Carbs" option is highlighted as the first sort option 1254, and the "Low-high" option is highlighted as the second sort option 1256. After defining the sort order in the sort sub-page 1252, the user may select to apply the sort order by selecting the check mark option 1258. It is appreciated that additional filtering may be performed following the logic presented above, such as for sugar, salt, cholesterol, etc.

Figure 17:
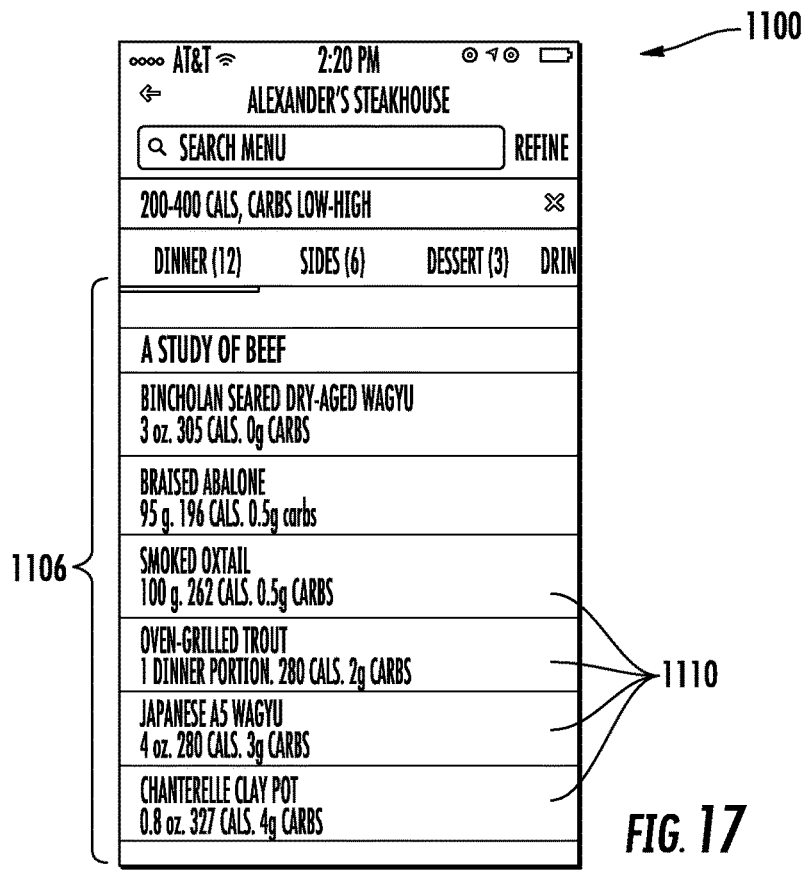
FIG. 17 is a representation of an exemplary user interface showing the restaurant menu view controller of FIG. 11 following application of the sort order of FIG. 16.

With a filter range defined by one of the filter options 1210, and a sort order defined in the sort sub-page 1252, the user may apply the defined filter range and sort order to the selected menu. In particular by selecting the "apply" option 1240 at the top of the filter page 1200, the user is returned to the menu listing 1106 of the restaurant menu view controller, as shown in FIG. 17. Once again, the user is presented with the "Alexander's Steakhouse" dinner menu listing 1106, including a number of menu items 1110. Because the dinner menu has been filtered, the only menu items listed are between 200 and 400 calories, as defined by the user via the "calories" filter option on the filter page 1200. All menu items previously listed in association with the "Alexander's Steakhouse" dinner menu that fall outside of the defined 200-400 calorie range are not included in the menu listing 1106. Therefore, some of the menu items 1110 included in the original menu listing 1106 of FIG. 11 will typically not be included in the filtered menu listing 1106 of FIG. 17. The menu listing 1106 of FIG. 17 is therefore a revised menu listing that includes list of menu items 1110 that is a subset of the list of menu items 1110 in the menu listing 1106 of FIG. 11.

In addition to the filtered menu listing being a subset of the original menu listing, the menu items 1110 in the filtered menu listing 1106 of FIG. 17 may include additional nutritional information that was not included with the menu items in the original menu listing 1106 of FIG. 11. For example, because the user defined the sort order for the menu to be based on "carbohydrates" (see FIG. 16), each menu item 1110 in FIG. 17 now includes an indication of carbohydrate count (e.g., the "Smoked Oxtail" menu item in FIG. 17 indicates 1.5 g carbs, while in FIG. 11 the "Smoked Oxtail" menu listing did not list any associated carbohydrates). Moreover, because the user defined the carbohydrate sort order to be from "low-to-high", the menu items 1110 in the menu listing 1106 of FIG. 17 are arranged based on an ascending carbohydrate value. Accordingly, the menu items 1110 in the filtered and sorted menu listing 1106 of FIG. 17 is arranged in an order that is different from that of the original menu listing 1106 of FIG. 11. The order of the original menu listing 1106 of FIG. 11 may be a restaurant-defined order as provided by the menu records 256. However, the filtered and sorted menu listing 1106 of FIG. 17 is a user-defined order based on ascending or descending order of the nutritional values associated with each menu item 1110 in the menu listing 1106.

As explained above, after entering filter metrics in the filter page 1200, the user is presented with a menu listing 1106 in FIG. 17 wherein all the menu items 1110 presented to the user will fit within the defined range (e.g., between 200 and 400 calories). The menu listing 1106 also provides a secondary benefit of sorting the menu items as defined by the user, such that the most desirable or beneficial menu items are presented first or higher in the list to the user (e.g., those menu items with the lowest carbohydrate count), and the menu items that are less desirable are presented later or lower in the list to the user (e.g., the menu items with the largest carbohydrate count).

In view of the foregoing, it will be recognized that the menu filter page 1200 provides the user with a tool that facilitates more efficient presentation of data to the user, including the ability to filter the menu items 1110 on a menu listing 1106, and also sort those filtered menu items as defined by the user. This arrangement saves valuable resources by more quickly and efficiently presenting the desired menu data to the user. The resources saved by the user include reduced data usage on the associated health tracking device, which is of particular value to users who have access to only limited amounts of data transfer over a period of time. Moreover, because users are able to obtain desired data quickly and more efficiently, the battery life of the associated health tracking device 110 is extended as users spend less time with the display illuminated as the user methodically moves through useless data that would otherwise be presented to the user without the filter arrangement described herein.

Figure 18:
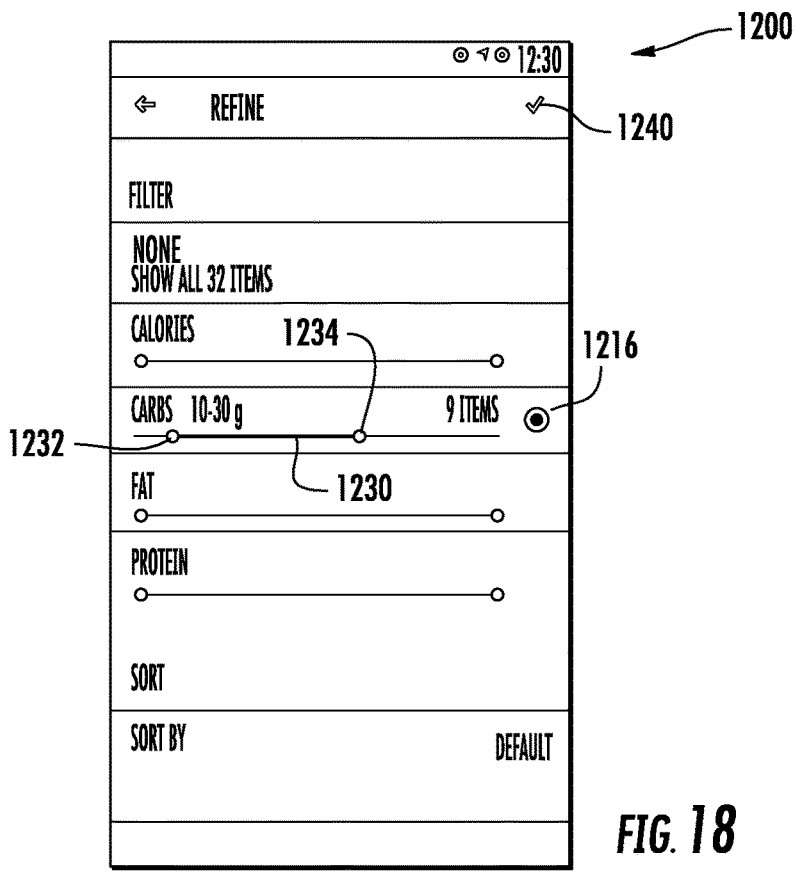
FIG. 18 is a representation of an exemplary user interface showing the filter page of FIG. 12 with a carbohydrate filter selected.

In addition to the foregoing, it will be recognized that the filter arrangement may further include additional features to assist the user in effectively and efficiently arriving at menu data. For example, as noted previously, in at least one embodiment, the user is provided if the user upgrades to a premium level of service, the user may define macronutrient filter parameters in addition to only calorie filter parameters. FIG. 18 shows an example of such an arrangement wherein the user is presented with a range bar 1230 associated with the "carbohydrates" filter option presented in block 1216. In the embodiment of FIG. 18, the user has manipulated the lower end slider 1232 and the upper end slider 1234 to define a carbohydrate range between 10 g and 30 g. By applying this filter to the menu listing 1106, the user will filter out all menu items 1110 that fall outside of the defined 10 g-30 g range. In at least one embodiment, the user may apply only a single filter to the menu listing 1106. In this embodiment, only one of the "calories," "carbohydrates," "fat," or "protein" filter options may be selected at a time, and selection of a subsequent filter option will deselect a previously selected filter option. However, in at least one embodiment, the user may select multiple filter options and use the range bar to define a range for each filter option. For example, the user may define a calorie range between 200 and 400 calories, a carbohydrate range between 10 g and 30 g, and a fat range between 5 g and 15 g, and this apply all of these filters to the menu listing 1106. In this manner, the user is presented with an even more efficient tool for the management and presentation of menu data via the health tracking device 110. However, it is appreciated that in in this embodiment, a selected range of carbohydrates, fat, protein, etc. may require at least a minimum caloric value, hence the calories may be automatically updated as the user enters one or more of the previously described ranges.

Figure 19:
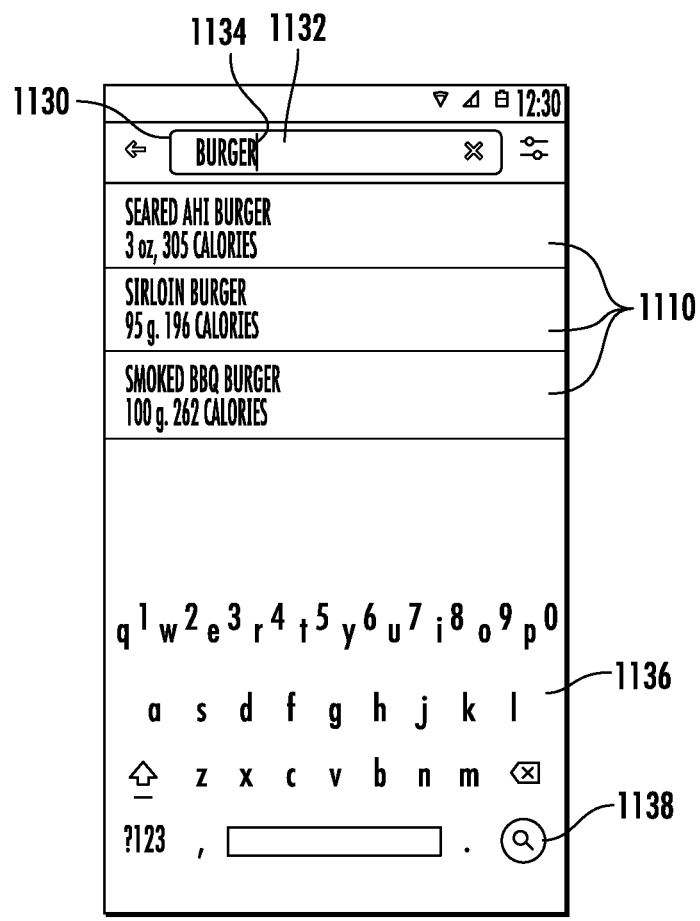
FIG. 19 is a representation of an exemplary user interface showing a search page of the restaurant menu view controller of FIG. 11.

Yet another example of an additional feature that may be used to assist the user in effectively and efficiently arriving at menu data is the menu search option 1130 shown in FIG. 11. When the menu search option 1130 is selected, a curser 1132 is presented in a search text block 1134, as shown in FIG. 19, and the user is presented with a keyboard 1136. The user may then type, say, or otherwise enter a particular item the user is interested in viewing from the menu listing 1106. For example, in FIG. 19, the user typed the search term "Burger" into the text block 1134. After applying the search term the search icon 1138, the health tracking system searches for all menu listings that match the entered search term. In this case, three menu items 1110 match the search term. The user may then review these menu items and determine whether he or she is interested in consuming one of the menu items. Advantageously, because the user knew of a particular menu item of interest, the user could enter a search term in the search block 1134 and review only those menu items that match the search term.

The methods discussed herein may be accomplished with the assistance of a computer program, such as the network and/or client side health tracking programs described above. The above described system and method solves a technological problem common in industry practice related to effective and efficient entry and processing of menu data, including menu items and related nutritional data, and the related efficient presentation of menu data to the user. Moreover, the above-described system and method improves the functioning of the computer/device and particularly health tracking devices by not only presenting menu data, but also by restricting menu data that is presented to the user, and thereby reducing data usage and extending battery life for the health tracking device. Additionally, the above-described system and method improves the functioning of the computer/device and particularly health tracking devices by allowing menu data to be effectively communicated to the user along with a graphical user interface that facilitates the entry of filter metrics that are then applied to the menu data.

Portions of the system and methods described herein may be implemented using one or more programs or suitable software code, such as the network and/or client-side health tracking applications, described above, each of which may reside within the memory of the respective computing devices as software or firmware. Such programs and code may be stored in the memory and executed by the processor of the display device or a system server or other computer in communication with the display device. A computer program product implementing an embodiment disclosed herein may therefore comprise one or more computer-readable storage media storing computer instructions translatable by processing circuitry/logic, a CPU, or other data processing device to provide an embodiment of a system or perform an embodiment of a method disclosed herein. Computer instructions may be provided by lines of code in any of various languages as will be recognized by those of ordinary skill in the art.

A "computer-readable medium" may be any type of data storage medium that can store computer instructions and/or data, including, read-only memory (ROM), random access memory (RAM), hard disks (HD), data cartridges, data backup magnetic tapes, floppy diskettes, flash memory, optical data storage, CD-ROMs, or the like. The computer readable medium can be, by way of example, only but not by limitation, an electronic, magnetic, optical, electromagnetic, infrared, or semiconductor system, apparatus, system, device, or computer memory. The computer readable medium may include multiple computer readable media storing computer executable instructions, such as in a distributed system or instructions stored across an array. A "non-transitory computer-readable medium" may be any type of data storage medium that can store computer instructions, including, but not limited to the memory devices discussed above.

The above described system and method solves a technological problem common in industry practice of providing menu data from various restaurants to users of health tracking systems and assisting users in evaluating and organizing such menu data in an efficient manner. Moreover, the above-described system and method improves the functioning of the computer device by providing a menu filter that enables a user to quickly find and sort the most relevant menu data for the user. In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

The foregoing detailed description of one or more exemplary embodiments of the health tracking system has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:

1. A method of providing nutritional data to a user of a health tracking system, the method comprising:
   receiving a plurality of consumable records from a plurality of health tracking devices, wherein each of the plurality of consumable records includes at least nutritional data and a text string for a consumable item to which the consumable record relates, wherein a subset of the consumable records relate to a single menu item, and wherein the text string and the nutritional data are different for each consumable record in the subset of consumable records;
   storing the plurality of consumable records in a crowd-sourced database at a remote server;
   enabling the user to select a restaurant via one of the health tracking devices associated with the user, wherein said health tracking device includes a consumable log for the user comprising nutritional data entered by the user over a period of time;

generating first menu data based at least in part on the selected restaurant, the first menu data comprising a plurality of first menu items each having nutritional data associated therewith;

enabling the user to enter, via said one of the health tracking devices, a filtering metric by which the first menu data is filtered;

generating second menu data based at least in part on the filtered first menu data, the second menu data comprising a plurality of second menu items each having partial nutritional data associated therewith, the plurality of second menu items including the single menu item;

identifying from the crowd-sourced database a plurality of consumable record matches for each of the second menu items, wherein each of the plurality of consumable record matches includes supplemental nutritional data that is disparate from the partial nutritional data;

receiving a selection of the single menu item via the health tracking device;

displaying the plurality of consumable record matches identified for the selected second menu item on the health tracking device, wherein said consumable record matches comprise the subset of consumable records that relate to the single menu item;

receiving a selection of one of the displayed consumable record matches via the health tracking device; and in response to said selection, entering the nutritional data associated with said selected consumable record match in the consumable log for the user at said health tracking device.

2. The method of claim 1, wherein the second menu data comprises a subset of the first menu data which meet the filtering metric.

3. The method of claim 2, further comprising enabling the user to cause the second menu data to be sorted according to one or more of the nutritional data associated therewith.

4. The method of claim 1, wherein each of the plurality of data records comprises at least a text string descriptive of a consumable to which the data record relates, and wherein the nutritional data comprises at least caloric information and macronutrient information.

5. The method of claim 4, wherein the filtering metric comprises at least one of:
a filter based on the text string; and
a filter based on the caloric information and/or nutrition information.

6. The method of claim 1, wherein enabling the user to select a restaurant at a health tracking device of the health tracking system further comprises:
enabling the user to enter a search request at a health tracking device of the health tracking system;
providing a list of a plurality of restaurants identified based on the search request; and
wherein the act of enabling the user to select the restaurant comprises enabling the user to select one of the plurality of restaurants in the list.

7. The method of claim 6, wherein enabling the user to enter the search request includes receiving geo-location data for the user from the health tracking device, and the act of identifying the plurality of restaurants is based at least in part on the geo-location data.

8. The method of claim 1 wherein the consumable record matches for the are based at least in part on previously selected consumable records from the crowd-sourced database for the second menu items, and one or more of (i) the location of the user, (ii) the menu selected by the user, and (iii) a correlation between the name of the selected menu item and the title of a consumable record.

9. The method of claim 7 wherein the health tracking device is a GPS-enabled device configured to provide the geo-location data for the user.

10. A non-transitory computer readable medium for operating a health tracking system, the computer-readable medium having a plurality of instructions stored thereon that, when executed by a processor, cause the processor to:
provide a selectable list of restaurants to a user based at least in part on a proximity of a health tracking device associated with the user to said restaurants;
in response to a user's selection of one of the restaurants on the list, generate first menu data, the first menu data comprising a plurality of first menu items, each first menu item comprising a text string representative of the consumable item to which the first menu item relates and nutritional data associated to the consumable item;
provide a mechanism to enable the user to filter the first menu data according to at least one of the text string and/or the nutritional data thereof;
in response to the user's filter, generate second menu data, the second menu data comprising a plurality of second menu items each having partial nutritional data associated therewith;
identify from a crowd-sourced database a plurality of consumable record matches for each of the second menu items, wherein a subset of the plurality of consumable record matches includes at least nutritional data and a text string for one of said second menu items, wherein the text string and the nutritional data are different for each consumable record in the subset, and wherein each consumable record in the subset includes supplemental nutritional data that is disparate from the partial nutritional data;
receive a selection of said one of the second menu items; and
display the subset of the plurality of consumable record matches identified for the selected second menu item for display to the user on a health tracking device of the health tracking system.

11. The non-transitory computer readable medium of claim 10, wherein the plurality of instructions are further configured to, when executed by the processor, provide a mechanism to enable the user to set an order by which the second menu data is presented, the order being based at least in part on at least one of the text string and/or the nutritional data thereof.

12. The non-transitory computer readable medium of claim 10, wherein providing the selectable list of restaurants to a user based at least in part on a proximity of a health tracking device associated with the user to said restaurants includes the plurality of instructions being further configured to, when executed by the processor:
receive information from said health tracking device relating to a geographic location of the user;
utilize said information to identify a plurality of restaurants within a given distance of the geographic location of the user; and
provide the plurality of identified restaurants as the selectable list.

13. The non-transitory computer readable medium of claim 10, wherein the plurality of instructions are further configured to, when executed by the processor:
receive a search request from the use via a health tracking device;
execute the requested search; and
provide the results of the search as the selectable list.

14. The non-transitory computer readable medium of claim 10, wherein said health tracking device includes a daily log for the user comprising nutritional data entered by the user for each of a plurality of days, and wherein the plurality of instructions are further configured to, when executed by the processor:
   enable the user to select one of the subset of the plurality of consumable record matches; and
   in response to the selection thereof, add the nutritional data associated to the selection to the daily log for the user.

15. The non-transitory computer readable medium of claim 10, wherein the nutritional data comprises at least one of: caloric value and macronutrient values.

16. A network apparatus in a health tracking system comprising a plurality of health tracking devices, the plurality of health tracking devices including a user health tracking device, the network apparatus comprising:
   an interface configured to communicate with the plurality of health tracking devices and receive consumable records therefrom;
   a storage apparatus configured to store the received consumable records as part of a crowd-sourced database of consumable records, wherein each of the consumable records includes at least nutritional data and a text string for a consumable item to which the consumable record relates, wherein a subset of the consumable records relate to a single menu item, and wherein the text string and the nutritional data are different for each consumable record in the subset of consumable records; and
   a processor configured to execute a computer application comprising a plurality of instructions which are configured to, when executed, cause the network apparatus to:
      receive a selection of a restaurant from said user health tracking device;
      generate menu data relating to one or more consumable items at the selected restaurant, the menu data including a list of menu items and associated partial nutritional values for each menu item in the list, wherein the single menu item is included in the list of menu items;
      transmit the menu data to said user health tracking device;
      receive, from said user health tracking device, a selection of the single menu item from said list of menu items;
      identify, from the crowd-sourced database, the subset of consumable records that relate to the single menu item, wherein each of the consumable records in the identified subset of consumable records includes supplemental nutritional data that is disparate from the partial nutritional values associated with the single menu item;
      transmit the identified subset of consumable records to said user health tracking device for display thereat; and
      enter the supplemental nutritional data associated with a selected consumable record from said subset of consumable records into a daily log for the user.

17. The apparatus of claim 16, wherein said plurality of instructions are further configured to, when executed, cause the network apparatus to:
   generate a first list of menu items for said restaurant and associated partial nutritional values;
   receive, from said user health tracking device, an indication to filter the first list of menu items to only those ones associated with a desired nutritional value; and
   generate a second list of menu items that is a subset of the first list of menu items which are associated with the desired nutritional value.

18. The apparatus of claim 17, wherein the desired nutritional value comprises a range of acceptable values.

19. The apparatus of claim 17, wherein the first list of menu items is arranged in a first order and the second list of menu items is arranged in a second order that is different than the first order.

20. The apparatus of claim 17, wherein the user health tracking device is a global positioning system (GPS) enabled device, and wherein plurality of instructions are further configured to when executed, cause the network apparatus to:
   receive information relating to a geographic location of the user based on GPS data from the health tracking device;
   utilize said information to identify a plurality of restaurants within a given distance of the geographic location of the user; and
   provide the plurality of identified restaurants as a selectable list; and
   receive a selection by the user of one restaurant from the selectable list, the selected restaurant comprising the restaurant to which the menu data relates.

* * * * *